United States Patent
Schwab et al.

(10) Patent No.: US 7,202,075 B2
(45) Date of Patent: Apr. 10, 2007

(54) ISOLATED PROTEIN HAVING HYDROXYNITRILE LYASE ACTIVITY

(75) Inventors: Helmut Schwab, Graz (AT); Anton Glieder, Gleisdorf (AT); Christoph Kratky, Graz (AT); Ingrid Dreveny, Graz (AT); Rodolfo Bona, Graz (AT); Peter Pöchlauer, Linz (AT); Wolfgang Skranc, Vienna (AT); Herbert Mayrhofer, Engerwitzdorf (AT); Irma Wirth, Enns (AT); Rudolf Neuhofer, Engerwitzdorf (AT)

(73) Assignee: DSM Fine Chemicals Austria NFG GmbH & Co KG, Linz (AT)

(*) Notice: Subject to any disclaimer, the term of this patent is extended or adjusted under 35 U.S.C. 154(b) by 99 days.

(21) Appl. No.: 10/940,954

(22) Filed: Sep. 15, 2004

(65) Prior Publication Data

US 2005/0064552 A1  Mar. 24, 2005

Related U.S. Application Data

(62) Division of application No. 10/046,232, filed on Jan. 16, 2002, now Pat. No. 6,861,243.

(30) Foreign Application Priority Data

Jan. 16, 2001 (AT) ................................ A 60/2001
Apr. 3, 2001 (AT) ............................... A 523/2001

(51) Int. Cl.
*C12N 9/88* (2006.01)
*C12P 1/00* (2006.01)
*C07K 1/00* (2006.01)
*C07H 21/04* (2006.01)
*C07C 253/00* (2006.01)

(52) U.S. Cl. ..................... 435/232; 435/41; 435/183; 435/320.1; 530/350; 536/23.2; 558/351

(58) Field of Classification Search ................ 435/183, 435/232, 320.1, 41; 530/350; 536/23.2; 558/351
See application file for complete search history.

(56) References Cited

U.S. PATENT DOCUMENTS 6,046,042 A  4/2000  Hasslacher et al.

OTHER PUBLICATIONS

Cheng et al. Accession S32156. Nov. 22, 1993.*
M. Suelves, et al., "Molecular cloning of the cDNA coding for the (R)-(+)-mandelonitrile lyase of *Prunus amygdalus*: temporal and spatial expression patterns in flowers and mature seeds", *Planta*, vol. 206, pp. 388-393 (1998).
Z. Hu et al., "Molecular Analysis of (R)-(+)-Mandelonitrile Lyase Microheterogeneity in Black Cherry", *Plant Physiology*, vol. 119, pp. 1535-1546 (Apr. 1999).
Z. Hu et al., Accession U51562, Apr. 11, 1996.
ExPASy Home Page, "NiceZyme View of ENZYME: 4.1.2.10", Mandelonitrile lyase.
T. K. Atwood, et al., "Which craft is best in bioinformatics?", *Computers and Chemistry*, vol. 25, pp. 329-339 (2001).
C. P. Ponting, "Issues in predicting protein function from sequence", *Briefings in Bioinformatics*, vol. 2, No. 1, pp. 19-29 (Mar. 2001).

* cited by examiner

*Primary Examiner*—Tekchand Saidha
*Assistant Examiner*—Christian L. Fronda
(74) *Attorney, Agent, or Firm*—Wenderoth, Lind & Ponack, L.L.P.

(57) ABSTRACT

New genes containing a DNA sequence coding for hydroxynitrile lyase, which genes can be prepared via a primer combination based on the DNA sequence of the 5'-region of the mdl genes from the *Prunus serotina* and from *Prunus amygdalus* and/or a primer 2 based on the 3'-region of the DNA sequences of one of the hydroxynitrile lyase isoenzymes from *Prunus serotina* or from *Prunus amygdalus*, subsequent amplification with a DNA polymerase using a DNA from organisms, containing genes coding for hydroxynitrile lyase, as templates and cloning, and also recombinant proteins which can be prepared in suitable host cells by heterologous expression of the DNA sequence of said HNL genes, and proteins and fusion proteins derived therefrom and use of said proteins for preparing (R)- or (S)-cyanohydrins.

12 Claims, 12 Drawing Sheets

Figure 1

Nucleotide sequence of the *Prunus amygdalus* HNL5 gene obtained by PCR amplification

| | |
|---|---|
| 1 | GGAATTCACA ATATGGAGAA ATCAACAATG TCAGTTATAC TATTTGTGTT |
| 51 | GCATCTTCTT GTTCTTCATC TTCAGTATTC AGAGGTTCAC TCGCTTGCCA |
| 101 | ATACTTCTGC TCATGgtaaa tttccatctt cagtattcat ttaacagcaa |
| 151 | aatgtgtaga tttataatta agaaaactga cacaagtagt gcaagaaaca |
| 201 | agctaattta gatgcatgtt gaaaaaaatc tttcatctct tcacatatat |
| 251 | tttgcagATT TTAGCTACTT GAAGTTTGTG TACAACGCCA CTGATACAAG |
| 301 | CTCGGAAGGA TCATATGACT ACATTGTAAT CGGTGGAGGA ACATCAGGGT |
| 351 | GTCCATTGGC AGCAACTTTA TCAGAAAAAT ACAAGGTGCT TCTTCTAGAA |
| 401 | AGAGGCACTA TTGCTACAGA ATACCCGAAC ACGTTGACTG CAGATGGGTT |
| 451 | TGCATATAAT CTGCAGCAAC AAGATGATGG AAAGACGCCA GTTGAAAGGT |
| 501 | TCGTGTCCGA AGATGGCATT GATAATGTGC GAGCCAGGAT CCTCGGTGGC |
| 551 | ACGACCATAA TCAATGCAGG CGTCTACGCC AGAGCTAACA TTTCATTCTA |
| 601 | TAGTCAAACA GGAATTGAAT GGGACCTGGA TTTGGTCAAT AAGACATATG |

651  AGTGGGTTGA AGACGCCATT GTGGTCAAGC CAAATAATCA ATCTTGGCAA

701  TCTGTTATAG GAGAGGGATT CTTGGAGGCG GGTATTCTTC AGACAATGG

751  ATTTAGTTTG GATCACGAAG CAGGAACTAG ACTCACCGGC TCAACTTTTG

801  ACAATAATGG AACGCGACAT GCGGCTGATG AACTGCTTAA TAAAGGAGAC

851  CCTAATAACT TGCTAGTTGC AGTTCAGGCC TCAGTAGAGA AGATCCTCTT

901  CTCTTCCAAT ACATCAAgta tgttgcatca gtgatattta atggtagctc 951  ctagtttgtc atgctgcact cgaaaattat tattttatca tttttaaaata 1001 ctaacagaat agtgtgaagt ctcatattc cctccatat ttcccaaatt 1051 tccataaaca aaacttccca attctccttc gttagtttg acaataatta 1101 taagctattc tctaatgcag ATTTGTCAGC TATTGGAGTC ATATATACGG

1151 ATTCTGATGG AAACTCTCAT CAGGCATTTG TACGCGGTAA CGGAGAAGTT

1201 ATTGTTAGTG CAGGGACAAT CGGAACGCCT CAGCTTCTAC TACTTAGTGG

1251 CGTTGGACCA GAGTCTTACC TATCTTCTCT CAACATCACA GTTGTTCAGC

1301 CGAATCCTTA TGTTGGGCAG TTTGTGTATG ACAATCCTCG TAATTTCATT

1351 AATATTTTGC CCCCAAATCC AATTGAAGCC TCTGTTGTAA CTGTTTTAGG

1401 CATTAGAAGT GATTATTATC AAGTTTCTCT GTCAAGCTTG CCATTTTCCA

1451 CTCCACCCTT TAGTCTTTTT CCTACAACAT CTTACCCCCT CCCAAATTCG

1501 ACTTTTGCTC ATATTGTTAG CCAAGTTCCA GGACCATTGT CTCATGGTTC

1551 TGTCACGCTA AATTCATCAT CTGACGTGAG AATCGCTCCA AATATTAAAT

1601 TCAATTACTA TTCAAATTCC ACAGACCTTG CTAATTGTGT TAGCGGCATG

1651 AAGAAGCTTG GTGACTTATT AAGGACAAAG GCATTAGAAC CATATAAAGC

```
1701    TCGAGATGTG CTGGGAATTG ACGGTTTCAA TTATTTGGGA GTACCTTTGC

1751    CAGAGAACCA AACAGATGAT GCATCCTTCG AAACATTTTG TCTAGATAAT

1801    GTAGCTTCAT ACTGGCATTA CCACGGTGGA AGCCTTGTTC GGAAAGTGCT

1851    TGATGACAGT TTCCGTGTTA TGGGGATCAA AGCATTACGC GTTGTTGATG

1901    CCTCCACTTT CCCTTACGAA CCAAACAGCC ATCCTCAGGG CTTCTATCTG

1951    ATGTTAGGAA Ggtatgtgat gcacacttcc aaccactaga gattctcaat 2001    attttgttgt tgttgtaatg aactctctgc cgcattgctc ttttttatta 2051    atccttaaaa ttttgtgttt tgcgcagGTA TGTGGGCCTT CAAATCCTGC

2101    AAGAAAGGTC AATCCGGTTG GAGGCTATTC ATAATATTCA AGAGTCCATG

2151    TGAAGAATTC CG
```

*hnl5* coding region

Figure 3:

MEKSTMSVILFVLHLLVLHLQYSEVHSLA<u>NTS</u>AHDFSYLKFVY<u>NAT</u><u>D</u>TSSEGSYDYI
VIGGGTSGCPLAATLSEKYKVLLLERGTIATEYPNTLTADGFAYNLQQQDDGKTPVE
RFVSEDGIDNVRARILGGTTIINAGVYARA<u>NISF</u>YSQTGIEWDLDLV<u>NKT</u><u>Y</u>EWVEDAI
VVKPN<u>NQSW</u>QSVIGEGFLEAGILPDNGFSLDHEAGTRLTGSTFDN<u>NGT</u><u>R</u>HAADELL
NKGDPNNLLVAVQASVEKILFSS<u>NTS</u>NLSAIGVIYTDSDGNSHQAFVRGNGEVIVSA
GTIGTPQLLLLSGVGPESYLSSL<u>NIT</u>VVQPNPYVGQFVYDNPRNFINILPPNPIEASVV
TVLGIRSDYYQVSLSSLPFSTPPFSLFPTTSYPLP<u>NST</u><u>F</u>AHIVSQVPGPLSHGSVTL<u>N</u>
<u>SSS</u>DVRIAPNIKFNYYS<u>NST</u><u>D</u>LANCVSGMKKLGDLLRTKALEPYKARDVLGIDGFNY
LGVPLPE<u>NQT</u><u>D</u>DASFETFCLDNVASYWHYHGGSLVGKVLDDSFRVMGIKALRVVD
ASTFPYEPNSHPQGFYLMLGRYVGLQILQERSIRLEAIHNIQESM

Figure 4:

gaattcatcatgcagactctccttgtgagctcgcttgtggtctccctcgctgcggccctgcca-
cactacatcaggagcaatggcattgaagcctacaacgccactgatacaagctcggaaggatca-
tatgactacattgtaatcggtggaggaacatcagggtgtccattggcagcaactttatcagaa-
aaatacaaggtgcttcttctagaaagaggcactattgctacagaatacccgaacacgtt-
gactgcagatgggtttgcatataatctgcagcaacaagatgatggaaagacgccagttga-
aaggttcgtgtccgaagatggcattgataatgtgcgagccaggatcctcggtggcacgacca-
taatcaatgcaggcgtctacgccagagctaacatttcattctatagtcaaacaggaatt-
gaatgggacctggatttggtcaataagacatatgagtgggttgaagacgccattgtggt-
caagccaaataatcaatcttggcaatctgttataggagagggattcttggaggcggg-
tattcttccagacaatggatttagtttggatcacgaagcaggaactagactcaccggct-
caacttttgacaataatggaacgcgacatgcggctgatgaactgcttaataaaggagaccc-
taataacttgctagttgcagttcaggcctcagtagagaagatcctcttctcttccaatacat-
caaatttgtcagctattggagtcatatatacggattctgatgaaaactctcatcaggcatttg-
tacgcggtaacggagaagttattgttagtgcagggacaatcggaacgcctcagcttctac-
tacttagtggcgttggaccagagtcttacctatcttctctcaacatcacagttgttcagcc-
gaatccttatgttgggcagtttgtgtatgacaatcctcgtaatttcattaatatttttgcccc-
caaatccaattgaagcctctgttgtaactgttttaggcattagaagtgattattat-
caagtttctctgtcaagcttgccatttccactccaccctttagtctttttcctacaacatct-
tacccccctcccaaattcgactttgctcatattgttagccaagttccaggaccattgtct-
catggttctgtcacgctaaattcatcatctgacgtgagaatcgctccaaatattaaattcaat-
tactattcaaattccacagaccttgctaattgtgttagcggcatgaagaagcttggtgact-
tattaaggacaaaggcattagaaccatataaagctcgagatgtgctgggaattgacggttt-
caattatttgggagtacctttgccagagaaccaaacagatgatgcatccttcgaaa-
cattttgtctagataatgtagcttcatactggcattaccacggtggaagccttgttggga-
aagtgcttgatgacagtttccgtgttatggggatcaaagcattacgcgttgttgatgcctc-
cactttcccttacgaaccaaacagccatcctcagggcttctatctgatgttaggaagg-
tatgtgggccttcaaatcctgcaagaaaggtcaatgcagtgagcggccgcatgcgaattc Figure 5: Amino acid sequence of the hybrid protein PamHNL5xGOX, derived from the nucleic acid sequence (figure 4).

MQTLLVSSLVVSLAAALPHYIRSNGIEAYNATDTSSEGSYDYIVIGGGTSGCPLAATL
SEKYKVLLLERGTIATEYPNTLTADGFAYNLQQQDDGKTPVERFVSEDGIDNVRARI
LGGTTIINAGVYARANISFYSQTGIEWDLDLVNKTYEVVEDAIVVKPNNQSWQSVIG
EGFLEAGILPDNGFSLDHEAGTRLTGSTFDNNGTRHAADELLNKGDPNNLLVAVQA
SVEKILFSSNTSNLSAIGVIYTDSDGNSHQAFVRGNGEVIVSAGTIGTPQLLLLSGVG
PESYLSSLNITVVQPNPYVGQFVYDNPRNFINILPPNPIEASVVTVLGIRSDYYQVSLS
SLPFSTPPFSLFPTTSYPLPNSTFAHIVSQVPGPLSHGSVTLNSSSDVRIAPNIKFNY
YSNSTDLANCVSGMKKLGDLLRTKALEPYKARDVLGIDGFNYLGVPLPENQTDDAS
FETFCLDNVASYWHYHGGSLVGKVLDDSFRVMGIKALRVVDASTFPYEPNSHPQG
FYLMLGRYVGLQILQERSMQ

Figure 6:

```
PamHNL5Gox    1  mgtllvsslv vslaaalphy lrsngiea-- ---------- --YNATDTSS
PamHNL5       1  mekstmsvil fvlhllvlhl qysevhslan tsahdfsylk fvYNATDTSS PamHNL5Gox   37  EGSYDYIVIG GGTSGCPLAA TLSEKYKVLL LERGTIATEY PNTLTADGFA
PamHNL5      51  EGSYDYIVIG GGTSGCPLAA TLSEKYKVLL LERGTIATEY PNTLTADGFA PamHNL5Gox   87  YNLQQQDDGK TPVERFVSED GIDNVRARIL GGTTIINAGV YARANISFYS
PamHNL5     101  YNLQQQDDGK TPVERFVSED GIDNVRARIL GGTTIINAGV YARANISFYS PamHNL5Gox  137  QTGIEWDLDL VNKTYEWVED AIVVKPNNQS WQSVIGEGFL EAGILPDNGF
PamHNL5     151  QTGIEWDLDL VNKTYEWVED AIVVKPNNQS WQSVIGEGFL EAGILPDNGF PamHNL5Gox  187  SLDHEAGTRL TGSTFDNNGT RHAADELLNK GDPNNLLVAV QASVEKILFS
PamHNL5     201  SLDHEAGTRL TGSTFDNNGT RHAADELLNK GDPNNLLVAV QASVEKILFS PamHNL5Gox  237  SNTSNLSAIG VIYTDSDGNS HQAFVRGNGE VIVSAGTIGT PQLLLLSGVG
PamHNL5     251  SNTSNLSAIG VIYTDSDGNS HQAFVRGNGE VIVSAGTIGT PQLLLLSGVG PamHNL5Gox  287  PESYLSSLNI TVVQPNPYVG QFVYDNPRNF INILPPNPIE ASVVTVLGIR
PamHNL5     301  PESYLSSLNI TVVQPNPYVG QFVYDNPRNF INILPPNPIE ASVVTVLGIR PamHNL5Gox  337  SDYYQVSLSS LPFSTPPFSL FPTTSYPLPN STFAHIVSQV PGPLSHGSVT
PamHNL5     351  SDYYQVSLSS LPFSTPPFSL FPTTSYPLPN STFAHIVSQV PGPLSHGSVT PamHNL5Gox  387  LNSSSDVRIA PNIKFNYYSN STDLANCVSG MKKLGDLLRT KALEPYKARD
PamHNL5     401  LNSSSDVRIA PNIKFNYYSN STDLANCVSG MKKLGDLLRT KALEPYKARD PamHNL5Gox  437  VLGIDGFNYL GVPLPENQTD DASFETFCLD NVASYWHYHG GSLVGKVLDD
PamHNL5     451  VLGIDGFNYL GVPLPENQTD DASFETFCLD NVASYWHYHG GSLVGKVLDD PamHNL5Gox  487  SFRVMGIKAL RVVDASTFPY EPNSHPQGFY LMLGRYVGLQ ILQERSmg-
PamHNL5     501  SFRVMGIKAL RVVDASTFPY EPNSHPQGFY LMLGRYVGLQ ILQERSirle PamHNL5Gox  535  ---------
PamHNL5     551  aihniqesm
```

Figure 7: Analysis of HNL preparations by SDS PAGE. Details are described in example 11.
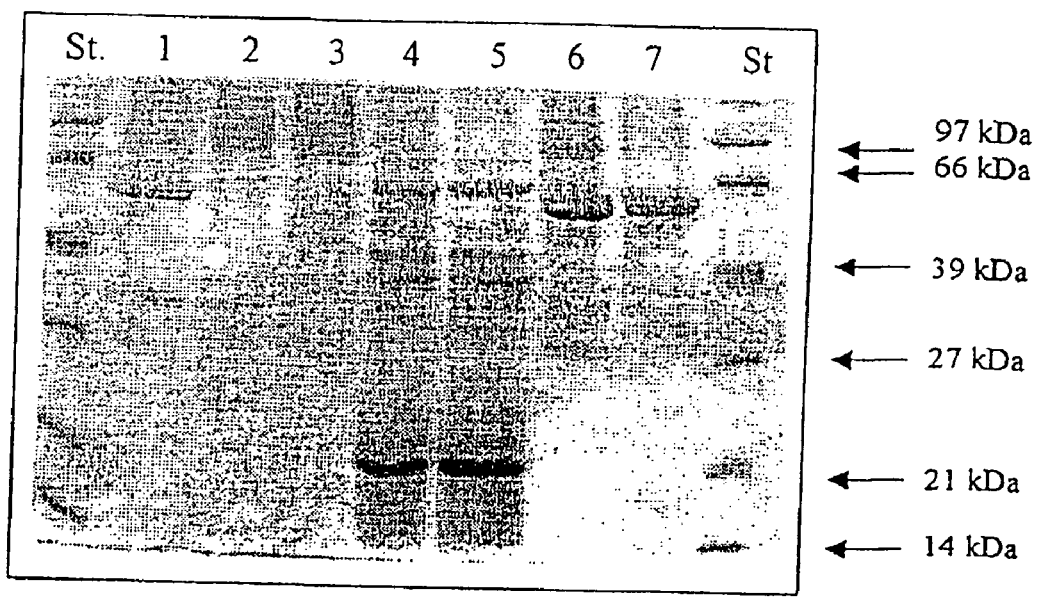

Figure 8:

Nucleotide sequence of the *Prunus amygdalus* HNL1 gene obtained by PCR amplification.

ATGGAGAAATCAACAATGTCAGCTATACTGTTGGTGTTATACATTTTTGTCCTCC
ATCTTCAATATTCTGAGGTCCACT
CGCTTGCCACGACTTCTGATCATGgtaaatcacttcaaccgtaattcaaaacaccaaaaagg-
caatcaaaaagaaaacg
gaaaaaagtgtaagaaaagcagatatagacgcctgcatagatgcatgtgctatatactttaaaaactcttcgtctctt
gagattttgcagATTTTAGCTACCTGAGCTTTGCATACGACGCCACTGATCTA-
GAGTTGGAAGGATCATATGACTACGT
TATAGTTGGCGGAGGAACATCAGGGTGTCCATTGGCAGCAACTTTATCAGAAAA
ATACAAGGTGCTCGTTCTCGAAAGG
GGCAGTCTTCCGACAGCATATCCCAACGTCTTGACTGCAGATGGGTTTGTATAT
AATCTCCAGCAAGAAGATGATGGAA
AGACACCGGTCGAAAGGTTCGTGTCCGAAGATGGTATTGATAATGTACGGGGC
AGGGTGCTCGGTGGCACAAGCATTAT
CAATGCCGGTGTCTACGCCAGAGCTAACACCTCAATCTATAGTGCATCAGGAGT
TGATTGGGACATGGATTTGGTTAAT
CAGACATATGAGTGGGTTGAAGACACTATTGTGTACAAGCCAAATTCTCAATCTT
GGCAGTCTGTTACAAAAACTGCAT
TCTTGGAGGCTGGTGTTCATCCAAACCATGGATTTAGTTTAGATCATGAAGAAG
GAACTAGAATTACCGGCTCAACTTT
TGACAACAAGGGAACGAGACATGCAGCTGATGAACTTCTTAATAAAGGAAACTC
TAACAACTTGCGAGTTGGAGTTCAT
GCCTCAGTAGAGAAGATCATCTTCTCCAATGCACCAGgtatgttgcatcatgcactccaa-
aattaatatttgtcattt
taaaacactagcaggagccaaggtctggaagtacgaataaaatttcattattttccttggatttgtttgataatgatta
taagctttctgtaatgtagGTTTGACAGCTACAGGAGTCATATATAGGGATTCTAATG-
GAACGCCTCACCAAGCATTT
GTACGCAGTAAGGGAGAAGTTATCGTGAGTGCAGGGACAATTGGGACCCCTCA
ACTTCTACTACTTAGCGGTGTTGGGC CAGAGTCTTACCTATCATCTCTAAATATTCCAGTTGTTCTTTCCCATCCTTACGTC
GGACAGTTTCTGCATGACAATCC
TCGTAATTTCATTAACATTTTGCCCCCAAATCCAATTGAACCCACAATTGTAACTG
YTCTAGGCATTTCAAACGATTTC
TACCAATGTTCTTTCTCGAGCTTGCCATTTACAACTCCACCCTTCGGTTTTTTCC
CTAGTGCATCTTATCCCTGCCAA
ATTCGACTTTTGCTCACTTTGCTAGCAAAGTGGCAGGACCTTTATCATATGGTTC
TCTCACACTGAAATCATCCTCCAA
TGTGAGAGTCAGTCCAAATGTCAAATTTAATTACTATTCAAATCTGACAGATCTTT
CTCATTGTGTTAGCGGCATGAAG
AAGATTGGTGAACTCTTGAGCACAGACGCATTAAAACCATATAAAGTTGAAGATT
TGCCGGGTGTAGAAGGTTTTAATA
TTTTGGGAATCCCTTTGCCAAAGGACCAAACAGATGATGCAGCCTTCGAAACAT
TTTGCCGAGAATCAGTAGCCTCATA
TTGGCACTACCACGGTGGATGCCTTGTTGGAAAGGTGCTTGATGGTGATTTCCG
TGTTACAGGGATCAATGCATTACGC
GTTGTTGATGGCTCAACATTCCCTTACACACCAGCGAGCCACCCTCAGGGCTTC
TATCTGATGTTAGGGAGgtatgtta
caaattctcaataattatttggttgagtggcttgttgtaatgaactctatgccatatttctcttctcatcctttcca
tttttgtgccatgggcagGTATGTGGGCATTAAAATTCTGCAAGAAAGATCAGCTTCA-
GATCTAAAAATCTTGGATTCC
CTCAAGTCAGCAGCATCCTTGGTTCTTTAAACT

Figure 9:

Amino acid sequence of *Prunus amygdalus* hydroxynitrile lyase (HNL1), derived from the nucleotide sequence of the *HNL1* gene.

MEKSTMSAILLVLYIFVLHLQYSEVHSLATTSDHDFSYLSFAYDATDLELEGSY
DYVIVGGGTSGCPLAATLSEKYKVLVLERGSLPTAYPNVLTADGFVYNLQQE
DDGKTPVERFVSEDGIDNVRGRVLGGTSIINAGVYARANTSIYSASGVDWDM
DLVNQTYEWVEDTIVYKPNSQSWQSVTKTAFLEAGVHPNHGFSLDHEEGTRI
TGSTFDNKGTRHAADELLNKGNSNNLRVGVHASVEKIIFSNAPGLTATGVIYR
DSNGTPHQAFVRSKGEVIVSAGTIGTPQLLLLSGVGPESYLSSLNIPVVLSHPY
VGQFLHDNPRNFINILPPNPIEPTIVTVLGISNDFYQCSFSSLPFTTPPFGFFPS
ASYPLPNSTFAHFASKVAGPLSYGSLTLKSSSNVRVSPNVKFNYYSNLTDLSHC
VSGMKKIGELLSTDALKPYKVEDLPGVEGFNILGIPLPKDQTDDAAFETFCR
ESVASYWHYHGGCLVGKVLDGDFRVTGINALRVVDGSTFPYTPASHPQGFYL
MLGRYVGIKILQERSASDLKILDSLKSAASLVL

US 7,202,075 B2

ISOLATED PROTEIN HAVING HYDROXYNITRILE LYASE ACTIVITY

This application is a divisional of Ser No. 10/046,232, filed, Jan. 16, 2002 now U.S. Pat. No. 6,861,243.

BACKGROUND OF THE INVENTION

1. Field of the Invention

Biocatalytic processes have become very important for the chemical industry. In this connection, carrying out chemical reactions with the aid of biological catalysts is particularly interesting in those fields of application in which it is possible to utilize the frequently found enzyme property of preferably converting or forming in chemical reactions with chiral or prochiral components one of the two enantiomers.

Essential requirements for utilizing said advantageous properties of enzymes are the availability of said enzymes in industrially required amounts and a sufficiently high reactivity and also stability under the real conditions of an industrial process.

2. Description of the Related Art

Cyanohydrins are a particularly interesting class of chiral chemical compounds. Cyanohydrins are important, for example, in the synthesis of α-hydroxy acids, α-hydroxyketones, β-aminoalcohols which are used for producing biologically active substances, for example pharmaceutical active substances, vitamins or pyrethroid compounds.

Said cyanohydrins are prepared by addition of hydrocyanic acid to the carbonyl group of a ketone or aldehyde.

Industrial production of chiral compounds such as, for example, (S)-cyanohydrins was made possible by making use of the enzyme (S)-hydroxynitrile lyase from *Hevea brasiliensis* and is described, for example, in WO 97/03204, EP 0 951561 and EP 0 927 766.

However, there is a large variety of interesting chemical compounds for which the R enantiomers are important for industrial applications. Up until now, only processes which can be used only on the laboratory scale have been described for preparing a number of products (e.g.: EP 0 276 375, EP 0 326 063, EP 0 547 655). In this connection, mainly enzyme preparations obtained from plants of the Rosaceae family, for example from the kernels of almonds (*Prunus amygdalus*), were used.

Recently, *Prunus* species have become more and more important so that attempts were made to investigate said species in greater detail.

The specialist literature, for example Plant Physiology, April 1999, Vol 119, pp. 1535–1546, discloses that *Prunus* species can contain a plurality of R-HNL isoenzymes. These isoenzymes are expressed at different levels in various tissues of the plant. It was possible to identify in the plant *Prunus serotina* which is a close relative of *Prunus amygdalus* 5 different isoenzymes up until now and to sequence their genes. Only one *Prunus amygdalus* isoenzyme has been described up until now in Planta (1998) 206: 388–393, and this isoenzyme is most strongly expressed in the flower bud. A gene for said R-HNL isoenzyme has already been isolated and the cDNA has been sequenced.

However, no successful (functional) heterologous expression of such a gene has been reported in the specialist literature or patent literature.

Industrial applications on a large scale, too, have not been carried out up until now, the main reason being that enzyme preparations from almond kernels with hydroxynitrile lyase activity have not been available up until now in sufficient quantities and at justifiable costs.

SUMMARY OF THE INVENTION

It was therefore an object of the invention to create a basis which can provide an R-hydroxynitrile lyase in amounts required for industrial applications.

This object was achieved by looking for a way of producing an enzyme corresponding to the R-HNL preparation of *Prunus amygdalus* by genetic engineering strategies with the aid of an appropriate recombinant microorganism strain. Such a recombinant enzyme with R-HNL activity ought to be made technically available in this way in a sufficient amount.

It can be derived from the DNA sequences described in the literature above that particular regions in the genes of the various isoenzymes are highly conserved. According to the invention, this is used as a basis for generating primers for PCR amplification of *P. amygdalus* R-HNL. With the aid of such primers it is then possible, using DNA isolated from for example almond kernels (*P. amygdalus*) as template, to amplify by means of PCR DNA pieces which show in the analysis by agarose gel electrophoresis distinct specific bands. According to the invention, bands were found which correspond to the size of mdl genes (Planta (1998) 206: 388–393). Subsequently, appropriate primers for all isoenzymes known in *Prunus serotina* are generated and corresponding PCR products are obtained. DNA from this region is isolated from appropriate preparative agarose gels and cloned into standard vectors for cloning of PCR-generated fragments in *Escherichia coli*.

Sequence analysis of a series of selected clones revealed the presence of clones with homologies to the particular, already known R-HNL genes of *Prunus* species, although the sequences of the clones or genes obtained in this way differ in several sequence positions from the sequences already known or published, whereby important functional differences are established.

As a result, a new variant of HNL genes was unexpectedly found, although primer combinations which made use of the already known sequence of a cDNA obtained from *Prunus amygdalus* flower material were used.

The new genes were sequenced and the genomic DNA sequence was determined.

Accordingly, the present invention relates to new genes containing a DNA sequence coding for hydroxynitrile lyase, which genes can be prepared via a primer combination of a primer 1 based on the DNA sequence of the 5'-region of the mdl genes from *Prunus serotina* and from *Prunus amygdalus* and/or a primer 2 based on the 3'-region of the DNA sequences of one of the hydroxynitrile lyase isoenzymes from *Prunus serotina* or from *Prunus amygdalus*, subsequent amplification with a DNA polymerase using a DNA from organisms, containing genes coding for hydroxynitrile lyase, as templates and cloning.

Thus it is possible, for example, to prepare gene-specific PCR primer based on sequence homology of the *Prunus amygdalus* MDL1 gene and of the *Prunus serotina* mdl5 gene, and, as a result, a new gene, the HNL5 gene, is obtained after amplification and cloning.

BRIEF DESCRIPTION OF THE DRAWINGS

FIG. 1 shows the nucleotide sequence (SEQ ID No. 19) of the *Prunus amygdalus* HNL5 gene obtained by PCR amplification. The start codon (ATG) and stop codon of the open reading frame are printed in bold type, and the nucleotides in the intron regions are indicated in lower case letters. The peripheral sequences which have been attached via the PCR primers and which are not part of the HNL5 gene are underlined. The splice sites of the introns were identified with the aid of the consensus sequence "GT . . . AG".

FIG. 3 shows the amino acid sequence (SEQ ID No. 20) of the *Prunus amygdalus* hydroxynitrile lyase (HNL5), derived from the nucleotide sequence of the HNL5 gene (SEQ ID No. 19). The signal sequence determined from sequence analysis is printed in bold type and the postulated processing site is indicated by an arrow. Possible glycosylation sites (PROSITE patterns) are underlined.

FIG. 4 shows the nucleic acid sequence (SEQ ID No. 21) of the DNA fragment coding for a secretory hybrid protein (PamHNL5xGOX) with HNL activity, consisting of sequences of the *Prunus amygdalus* HNL5 gene and the *Aspergillus niger* glucose oxidase gene.

FIG. 5 shows the amino acid sequence (SEQ ID No. 22) of the hybrid protein PamHNL5xGOX, derived from the nucleic acid sequence (SEQ ID No. 21) of FIG. 4.

FIG. 6 shows the comparison of the amino acid sequences of *Prunus amygdalus* HNL5 (SEQ ID No. 20) and of the hybrid protein PamI-HNL5xGOX (SEQ ID No. 22). Sequence parts of *Aspergillus niger* glucose oxidase are underlined. Sequence regions having no significant homology between the two proteins are printed in italics, and the signal peptides are printed in bold type.

FIG. 7 shows the analysis of HNL preparations by SDS PAGE. Details are described in Example 11.

FIG. 8 shows the nucleotide sequence (SEQ ID No. 23) of the *Prunus amygdalus* HNL1 gene obtained by PCR amplification.

FIG. 9 shows the amino acid sequence (SEQ ID No. 24) of *Prunus amygdalus* hydroxynitrile lyase (HNL 1), derived from the nucleotide sequence of the HNL1 gene (SEQ ID No. 23).

DESCRIPTION OF THE PREFERRED EMBODIMENTS

Figure 2:
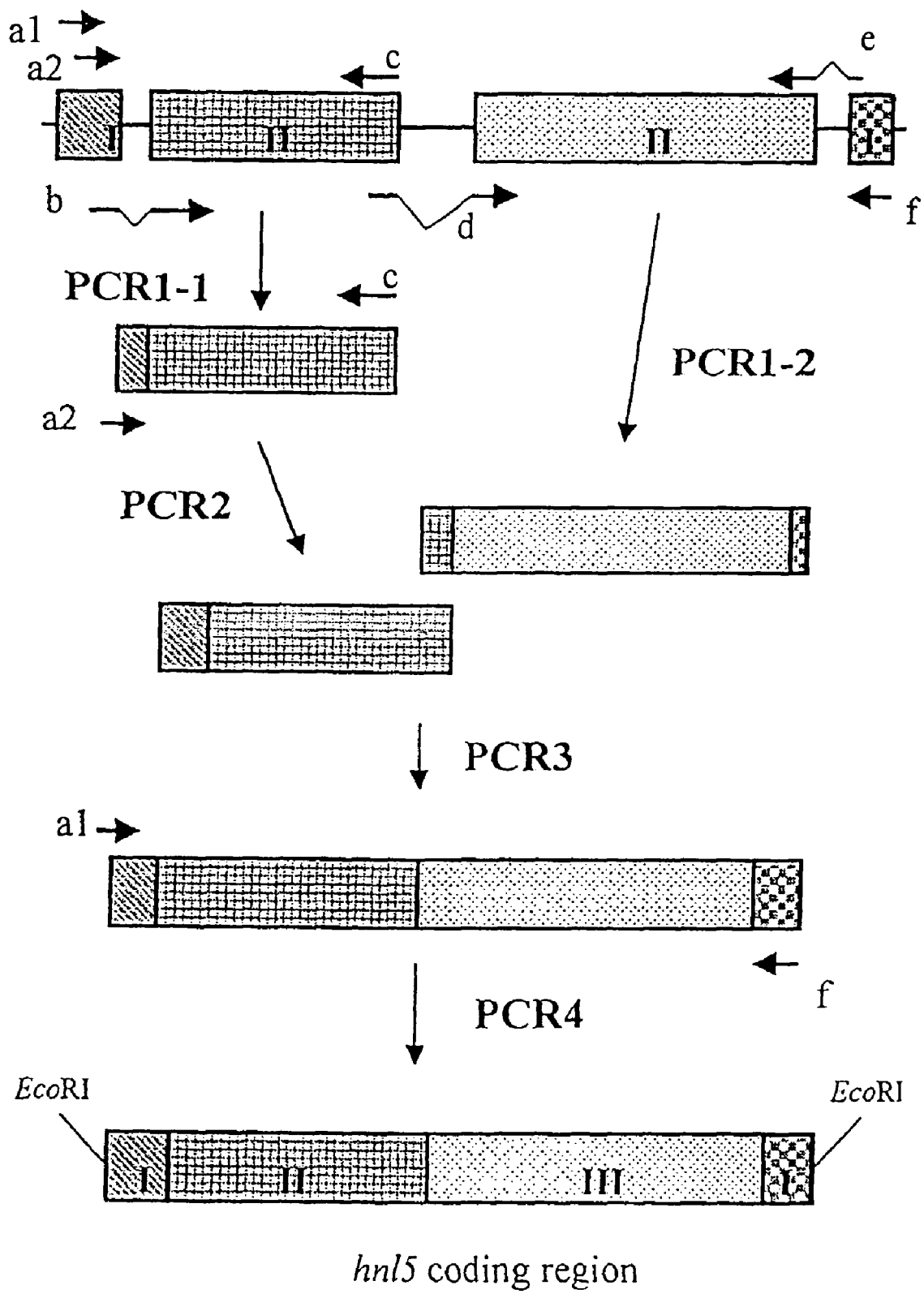
FIG. 2 shows an intron-free *Prunus amygdalus* HNL5 gene being obtained by PCR splicing. By means of a specific PCR strategy using overlapping primers, the coding regions were linked to one another by 4 successive PCR reactions.

The *Prunus amygdalus* HNL5 gene produced by PCR amplification, for example, has the nucleotide sequence depicted in FIG. 1, which is likewise a subject of the invention. The invention also relates to HNL5 genes having a nucleotide sequence which is at least 80%, preferably 85%, identical to the sequence depicted in FIG. 1.

The new HNL5 gene differs from the published sequence of the *Prunus amygdalus* MDL 1 gene in 7 base pairs.

Furthermore it is possible, for example, to prepare gene-specific PCR primers based on sequence homology of the *Prunus serotina* mdl1 gene, and, as a result, a new gene, the HNL1 gene, is obtained after amplification and cloning.

The HNL1 gene produced by PCR amplification, for example, has the nucleotide sequence depicted in FIG. 8, which is likewise a subject of the invention. The invention also relates to HNL1 genes having a nucleotide sequence which is at least 80%, preferably 85%, identical to the sequence depicted in FIG. 8.

Analogously, it is possible, according to the invention, to prepare further gene-specific PCR primers, for example based on the sequence of the *Prunus amygdalus* MDL1 gene and/or based on the sequence of the known *Prunus serotina* mdl1, mdl2, mdl3 and mdl4 genes, and this results in obtaining, after amplification and cloning, further new genes such as, for example, HNL2, 3 or 4 which are all subjects of the present invention.

The genomic clones and genomic DNA thereof form the basis for obtaining enzyme preparations by heterologous expression, for example by inducible or constitutive expression, in various host cells.

Furthermore, sequence analysis of the genomic DNA of the new genes of the invention shows that the proteins encoded by the new genes possess a signal sequence or a signal peptide, and this also makes secretory expression of heterologous proteins in suitable host cells possible.

In this connection, specific expression vectors are used for expressing the protein of one of the cloned new genes as a fusion protein with a signal peptide.

Accordingly, the present invention further relates to recombinant proteins which can be prepared in suitable host cells by heterologous expression of the genomic DNA sequence of the *Prunus amygdalus* HNL genes (for example HNL1, HNL2, HNL3, HNL4 and HNL5). Examples of suitable host cells in this connection are microorganisms. Preference is given to eukaryotic microorganisms and particular preference is given to fungi. Examples are *Saccharomyces cerevisiae* or *Pichia pastoris*.

For example, the amino acid sequence of *Prunus amygdalus* hydroxynitrile lyase HNL5, derived from the nucleotide sequence of the HNL5 gene, is depicted in FIG. 3 and the amino acid sequence of *Prunus amygdalus* hydroxynitrile lyase HNL1, derived from the nucleotide sequence of the HNL1 gene, is depicted in FIG. 9.

In addition, the invention relates to the use of a DNA sequence which codes for the signal peptide of a hydroxynitrile lyase, for example of *Rosacea* species, for secretory expression of heterologous proteins in host cells and to the proteins obtained in this way.

Accordingly, the invention further relates to fusion proteins or heterologous proteins which can be prepared by using a DNA sequence which codes for the signal peptide of a hydroxynitrile lyase, for example of *Rosacea* species, and by secretory expression of said DNA sequence in suitable host cells.

Examples of suitable host cells in this connection are again microorganisms. Preference is given to bacteria or eukaryotic microorganisms, and particular preference is given to fungi, such as, for example, *Saccharomyces cerevisiae* or *Pichia pastoris*.

For example, the nucleic acid sequence of the DNA fragment coding for a secretory hybrid protein (PamHNL5xGOX) with HNL activity, which nucleic acid sequence comprises sequences of the *P. amygdalus* HNL5 gene and the *Aspergillus niger* glucose oxidase gene, is depicted in FIG. 4. The amino acid sequence of the PamHNL5xGOX hybrid protein, derived from the nucleotide sequence (FIG. 4), is depicted in FIG. 5.

FIG. 6 shows the comparison of the amino acid sequences of the *Prunus amygdalus* HNL5 protein and the PamHNL5xGOX hybrid protein.

In order to obtain the recombinant proteins of the invention, the clones, for example, which show homologies with the known genes of *P. amygdalus* MDL1 and/or with *P. serotina* mdl1, mdl2, mdl3, mdl4 and mdl5 are treated further.

In order to obtain recombinant proteins with hydroxynitrile lyase activity, the appropriate genes, for example the HNL5 gene, are incorporated, for example, into an expression vector for *Pichia pastoris* or for *Saccharomyces cerevisiae*.

The genomic DNA may be spliced beforehand by means of PCR. Preference is given to preparing a base fragment for constructing expression plasmids for heterologous expression of the appropriate gene in bacteria and eukaryotes. For this purpose, a plasmid is constructed from which it is possible to obtain a DNA fragment coding for a gene of the invention for incorporation into various expression vectors by cutting with restriction endonucleases.

Using the genes of the invention, it is thus possible to produce a functional HNL by expression in a heterologous host, using, for example, an inducible promoter system or a constitutively expressed promoter system.

It is thus possible to find, out of a large number of transformants, recombinant strains of, for example, *Pichia pastoris*, which overexpress recombinant protein with R-HNL activity. After inducing expression, the majority of the protein with R-HNL activity can be found in said strains in the culture supernatant.

Thus it was possible for the first time to prepare a recombinant protein which has an R-HNL activity comparable to that detectable in almonds (*Prunus amygdalus* kernels) in amounts usable for industrial applications.

Unexpectedly it was found that the recombinant proteins with R-HNL activity, which are derived, for example, from the HNL1–5 genes of the invention and are denoted Pam-HNL1–5, have, compared with the enzyme preparation isolated from almonds, substantially better properties as biocatalysts in reaction mixtures for the preparation of cyanohydrins and can thus be used particularly advantageously for biocatalytic synthesis of cyanohydrins.

Furthermore, it is also possible to truncate the sequences of the recombinant proteins of the invention at the C-terminal end or to replace the sequences in the N- and C-terminal region by those of a related protein with different functions. Accordingly, the invention also relates to proteins altered in this way.

The recombinant proteins are distinguished in particular also by having a host-specific glycosylation, as a result of which the recombinant proteins are substantially more stable than the native proteins.

A particular advantage of the recombinant proteins of the invention results from the substantially higher stability which causes a substantially lower amount of enzyme compared with the native enzyme to be required, in order to achieve high enantiomeric purity. Thus, comparative experiments show that, when using the recombinant proteins of the invention, merely a tenth of the required amount of native protein is required in order to achieve comparable enantiomeric purities (ee values).

Accordingly, the invention further relates to the use of the recombinant proteins of the invention (HNLs) for preparing (R)- or (S)-cyanohydrins.

The starting materials used for preparing the (R)- or (S)-cyanohydrins are an aldehyde or a ketone as substrate, a cyanide group donor and a recombinant protein of the invention.

Aldehydes mean in this connection aliphatic, aromatic or heteroaromatic aldehydes. Aliphatic aldehydes mean in this connection saturated or unsaturated, aliphatic, straight-chain, branched or cyclic aldehydes. Preferred aliphatic aldehydes are straight-chain aldehydes with in particular 2 to 30 carbon atoms, preferably from 2 to 18 carbon atoms, which are saturated or mono- or polyunsaturated. In this connection, the aldehyde may have both C—C double bonds and C—C triple bonds. The aliphatic, aromatic or heteroaromatic aldehydes may furthermore be unsubstituted or substituted with groups inert under the reaction conditions, for example with unsubstituted or substituted aryl or heteroaryl groups, such as phenyl, phenoxy or indolyl groups, with halogen, hydroxy, hydroxy-$C_1$–$C_5$-alkyl, $C_1$–$C_5$-alkoxy, $C_1$–$C_5$-alkylthio, ether, alcohol, carboxylic ester, nitro or azido groups.

Examples of aromatic or heteroaromatic aldehydes are benzaldehyde or differently substituted benzaldehydes such as, for example, 3,4-difluorobenzaldehyde, 3-phenoxybenzaldehyde, 4-fluoro-3-phenoxybenzaldehyde, hydroxybenzaldehyde, methoxybenzaldehyde, furthermore furfural, methylfurfural, anthracene-9-carbaldehyde, furan-3-carbaldehyde, indole-3-carbaldehyde, naphthalene-1-carbaldehyde, phthaldialdehyde, pyrazole-3-carbaldehyde, pyrrole-2-carbaldehyde, thiophene-2-carbaldehyde, isophthalaldehyde or pyridinaldehydes, thienylaldehydes etc.

Ketones are aliphatic, aromatic or heteroaromatic ketones in which the carbonyl carbon atom is substituted unequally. Aliphatic ketones mean saturated or unsaturated, straight-chain, branched or cyclic ketones. The ketones may be saturated or mono- or polyunsaturated. They may be unsubstituted or substituted with groups inert under reaction conditions, for example with unsubstituted or substituted aryl or heteroaryl groups such as phenyl or indolyl groups, with halogen, ether, alcohol, carboxylic ester, nitro or azido groups.

Examples of aromatic or heteroaromatic ketones are acetophenone, indolylacetone, etc.

Aldehydes and ketones which are suitable according to the invention are known or can be prepared as usual.

The substrates are converted in the presence of the HNLs of the invention using a cyanide-group donor.

Suitable cyanide group donors are hydrocyanic acid, alkali metal cyanides or a cyanohydrin of the general formula I

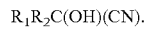

$R_1R_2C(OH)(CN)$.

In the formula I, $R_1$ and $R_2$ are independently of one another hydrogen or an unsubstituted hydrocarbon group, or $R_1$ and $R_2$ are together an alkylene group having 4 or 5 carbon atoms, where $R_1$ and $R_2$ are not simultaneously hydrogen. The hydrocarbon groups are aliphatic or aromatic, preferably aliphatic groups. $R_1$ and $R_2$ are preferably alkyl groups having 1–6 carbon atoms, and very preferably the cyanide group donor is acetonecyanohydrin.

The cyanide group donor may be prepared according to known methods. Cyanohydrins, in particular acetonecyanohydrin, may also be obtained commercially. Preference is given to using hydrocyanic acid (HCN), KCN, NaCN or acetonecyanohydrin as cyanide group donor, and particular preference is given to hydrocyanic acid.

In this connection, it is also possible to liberate hydrocyanic acid from one of its salts such as, for example, NaCN or KCN just prior to the reaction and to add it to the reaction mixture undissolved or in soluble form.

The conversion may be carried out in an organic, aqueous or 2-phase system or in emulsion. The aqueous system used is an aqueous solution containing the inventive HNL or a buffer solution. The examples thereof are Na citrate buffer, phosphate buffer, etc.

Organic diluents which may be used are aliphatic or aromatic hydrocarbons which are not or negligibly water-miscible and which are unhalogenated or halogenated, alcohols, ethers or esters or mixtures thereof. Preference is given to using methyl tert-butyl ether (MTBE), diisopropyl ether, dibutyl ether and ethyl acetate or a mixture thereof.

In this connection, the HNLs of the invention may be present either as such or immobilized in the organic diluent, but the conversion may also be carried out in a two-phase system or in emulsion using nonimmobilized HNL.

The present invention will now be described in more detail by the following Examples. However, the following Examples are merely illustrative in nature. Other Examples within the scope of the claims are also possible. Thus, the following should not be construed to limit the spirit and scope of the claims.

EXAMPLE 1

Isolation of Genomic DNA from Almonds (*Prunus Amygdalus* Kernels)

Dried almonds (Farmgold, batch number L4532, 1999 harvest) were finely chopped using a knife and frozen in a mortar with liquid nitrogen and ground using a pestle under liquid nitrogen to give a fine powder. 0.1 gram of frozen almond powder was directly admixed with 65° C. warm "breaking puffer" (100 mM NaAc; 50 mM EDTA; 500 mM NaCl, adjusted to pH 5.5; 1.4% SDS and 20 µg/ml RNAse A). After stirring for 15 minutes, the insoluble cellular residues were removed by centrifugation (10 min at 7000 g) and the supernatant was admixed with the same volume of 10 M ammonium acetate and then incubated on ice for 10 min. After centrifugation at 10,000 g for 15 minutes, the supernatant was extracted 2× with phenol/chloroform (1/1, phenol equilibriated with 50 mM Tris, pH 8.0). After another extraction with twice the volume of chloroform/isoamyl alcohol (24/1), the DNA was precipitated from the supernatant with the same volume of isopropanol, removed by centrifugation, and the DNA pellet was washed with 70% ethanol and dried in air. The DNA was then dissolved in 200 µl of water at 68° C. for 20 min and purified by ethanol precipitation (Ausubel et al., 1999). After the centrifugation, the DNA pellet was dried in air and dissolved in 50 µl of water.

EXAMPLE 2

Amplification and Cloning of a Genomic DNA Section of Almond (*Prunus Amygdalus*) DNA Homologous to Known *Rosaceae* mdl Genes Since it was known that a plurality of hydroxynitrile lyase isoenzymes whose sequences are highly homologous to one another can appear in *Prunus* species (Hu and Poulton, 1999), gene-specific PCR primers based on sequence homology of the *Prunus serotina* mdl5 gene and the *Prunus amygdalus* MDL1 gene (Suelves et al., 1998) were prepared:

```
Primer 1:                              (SEQ ID No. 1)
5'-CGGAATTCACAATATGGAGAAATCAACAATGTCAG-3'

Primer 2:                              (SEQ ID No. 2)
5'-CGGAATTCTTCACATGGACTCTTGAATATTATG-3'
```

The amplification was carried out in a 50 µl mixture with 1.2 U of "Hotstar" Taq DNA polymerase (Qiagen, Hilden, Germany), with 50 ng of genomic almond DNA as template, in each case 200 ng of primers 1 and 2, 5 µl of a dNTP (2 mM each) mix, all of these in 1×PCR buffer according to the "Hotstar Kit" manual (Qiagen, Hilden, Germany), starting with a denaturation step of 15 minutes at 95° C., followed by 30 cycles (1 min 95° C., 30 sec 64° C., 1 min 72° C.) for amplification and a final incubation at 72° C. for 5 min for preparation of complete products.

Said PCR produced a DNA fragment of approx. 2.16 kb in size (determined by analysis by means of agarose gel electrophoresis). This PCR product was purified by means of the "Qiaquick Kit" (Qiagen, Hilden, Germany) according to the enclosed manual and sequenced using the "Dye Deoxy Terminator Cycle Sequencing" kit (Applied Biosystems Inc., Forster City, Calif., USA) according to the primer walking strategy starting from the two primers used for the PCR. The obtained DNA sequence of the PCR fragment of 2162 base pairs total length is depicted in FIG. 1.

Approx. 0.5 µg of the purified PCR product was cut with restriction endonuclease EcoRI and cloned into plasmid vector pBSSK(−) (Stratagene Cloning Systems, La Jolla, Calif., USA) via the EcoRI cleavage site. The insert of a resultant recombinant molecule (the corresponding plasmid was denoted pBSPamHNL5g) was sequenced according to the method described above, and the sequence of the cloned fragment was 100% identical to the sequence of the above-described PCR product obtained with the two primers (1 & 2).

EXAMPLE 3

Sequence Analysis of the Genomic *Prunus Amygdalus* DNA Fragment Obtained by PCR Amplification with Primers 1 and 2.

In the region of the PCR-amplified and sequenced DNA section, an open reading frame which is interrupted by 3 introns was found. Said three introns were identified with the aid of the "GT . . . AG" intron consensus sequence. The reading frame starts with an ATG codon at position +13 and ends with a stop codon at position +2151.

For the coding region, the fragments of positions 13 to 115 (exon I), positions 258 to 917 (exon II), 1121 to 1961 (exon III) and 2078 to 2150 (exon IV) were joined together. The assembled DNA sequence codes for a protein with 559 amino acids and a calculated molecular weight of 61 kDa or 57.9 kDa for an N-terminally processed form. The peptide masses were calculated with the aid of the GCG program package (Genetics Computer Group, Wis., USA). Said protein was denoted PamHnl5.

The protein sequence derived for the open reading frame (without introns) is shown in FIG. 3. It was possible to determine distinctive homologies to known *Rosaceae* hydroxynitrile lyases (Blast program, GCG package, version 10.1, Genetics Computer Group, Wis., USA), the highest homologies being to the published sequences of *Prunus amygdalus* Mdl1 (99 percent identical, Suelves et al. 1998) and of *Prunus serotina* Mdl5 (94 percent identical, Hu and Poulton, 1999). With the aid of this homology, a cleavable signal sequence with cleavage between S27 and L28 was identified. It was possible to detect a cleavage site of this type in the two *Prunus serotina* Mdl1 and Mdl4 isoenzymes by N-terminal sequencing of the native proteins purified from plant material (Zihua Hu and Jonathan E. Poulton, Plant Physiology, 119, 1535–1546, 1999). The sequences of various HNL isoenzymes present in *Rosacea* species are known only for *Prunus serotina*. Due to the highest homologies to the *Prunus serotina* Mdl5 sequence, the new HNL gene from *Prunus amygdalus* was established as HNL5. Searching for sequence motifs in the PROSITE sequence motif database (GCG package, version 10.1, Genetics Computer Group, Wis., USA) revealed the presence of 13 potential N-glycosylation sites (drawn into FIG. 3).

EXAMPLE 4

Obtaining an intron-free *Prunus amygdalus* HNL5 gene by PCR splicing. By means of a specific PCR strategy using overlapping primers, the coding regions were linked to one another (according to FIG. 2) by 4 successive PCR reactions.

In the first round of PCR (PCR1-1 and PCR1-2) exons II and III were amplified using the primer pairs PamHNL5b/PamHNL5c (PCR1-1) and PamHNL5d/PamHNL5e (PCR1-2), respectively. The 50 µl PCR mixtures in 1× PCR buffer (Qiagen) contained: in each case 100 pmol of the appropriate primers, 2.5 U of "Hotstar" Taq DNA polymerase (Qiagen), 5 µl of a DNTP (2 mM each) mix, 10 ng of plasmid pBSPamHNL5g as template. The following program was run: 15 min 95° C., 30 cycles 1 min 95° C., 30 sec 68° C., 1 min 72° C., then finally 5 min 72° C. for preparation of complete products). After electrophoretic separation in an agarose gel, the products from PCR1-1 and PCR1-2 were eluted from the gel by means of the Qiaexll kit.

Amplification of approx. 50 ng of the product from PCR1-1 with in each case 100 pmol of primers PamHNL5a2 and PamHNL5c led to an extension of said first PCR product in the second round of PCR (PCR2). The following program was run: 15 min 95° C., 30 cycles 1 min 95° C., 30 sec 68° C., 1 min 72° C., then finally 5 min 72° C. for preparation of complete products). The other conditions were the same as for PCR1. After electrophoretic separation, this PCR product was likewise purified via an agarose gel and eluted.

In the third round of PCR (PCR3), the products from PCR1-2 and PCR2 were linked to one another by primer-less PCR with the aid of the overlapping ends (5 cycles of 1 min at 94° C., 30 sec at 68° C. and 1.5 min at 72° C., in each case approx. 100 ng of the two products from PCR1-1 and PCR2 in 50 µl mixtures in 1×PCR buffer (Qiagen), 5 µl of the dNTP (2 mM each) mix and 2.5 U of "Hotstar" Taq DNA polymerase (Qiagen).

The full length of the coding *Prunus amygdalus* hnl5 gene was completed and the complete product amplified in a fourth round of PCR (PCR4) using in each case 100 pmol of primers PamHNL5a1 and PamHNL5f. Said primers were directly added to the PCR 3 reaction mixture. The following program was run: 20 cycles of 1 min 95° C., 30 sec 63° C., 1.5 min 72° C. and, finally, 5 min 72° C.). The other conditions were the same as for PCR1.

The product obtained in the final round of PCR was fractionated via a preparative agarose gel and DNA of 1.6–1.8 kb in size was eluted from the gel by means of the "Quiaexll" kit (Qiagen) and cloned into plasmid pBSSK(-) via the EcoRI cleavage site. A clone having the correct restriction pattern was selected and sequenced.

The sequence in the coding region was 100% identical to the exons of the genomic DNA sequence. This clone was denoted pBSPamHNL5orf.

Oligonucleotide Primers

PamHnI5a1
5'-
GAAGATCTGAATTCCATGGAGAAATCAACAATGTCAGTTATACTATTTGT
GTTGCATCTTCTTG-3' (SEQ ID No. 3)

PamHnI5a2
5'-
CTATTTGTGTTGCATCTTCTTGTTCTTCATCTTCAGTATTCAGAGGTTCA
CTCGCTTGCCAATACTTC-3' (SEQ ID No. 4)

PamHnI5b
5'-
GTTCACTCGCTTGCCAATACTTCTGCTCATGATTTTAGCTACTTGAAGTT
TGTGTACAACGCCACTG-3' (SEQ ID No. 5)

PamHnI5c
5'-GATGTATTGGAAGAGAAGAGGATCTTCTCTACT-3'
(SEQ ID No. 6)

PamHnI5d
5'-
GATCCTCTTCTCTTCCAATACATCAAATTTGTCAGCTATTGGAGTCATAT
ATACGG 3' (SEQ ID No. 7)

PamHnI5e
5'-
CAACCGGATTGACCTTTCTTGCAGGATTTGAAGGCCCACATACCTTCCTA
ACATCAGATAGAAGCC-3' (SEQ ID No. 8)

PamHnI5f
5'-
GAAGATCTGGAATTCTTCACATGGACTCTTGAATATTATGAATAGCCTCC
AACCGGATTGACCTTTGTTGCAG-3' (SEQ ID No. 9)

EXAMPLE 5

The preparation of a base fragment for constructing expression plasmids for heterologous expression of the *Prunus amygdalus* HNL5 gene in bacteria and eukaryotes.

The aim of this experiment was to construct a plasmid from which a DNA fragment coding for *Prunus amygdalus* HNL5 for incorporation into various expression vectors can be obtained by restriction endonuclease cleavage. In this connection, PCR amplification added suitable sequences to the ends of the *Prunus amygdalus* HNL5 gene contained in pBSPamHNL5orf via appropriate primers.

The insert of plasmid pBSPamHNL5orf was amplified by means of PCR using the primers PCRHNL5-a and PCRHNL5-e (10 ng of DNA of plasmid pBSPamHNL5orf as template, 400 ng of primer PCRHNL5-a, 200 ng of primer PCRHNL5-e). The PCR reaction was carried out in 50 µl mixtures in 1×PCR buffer (Qiagen), containing 5 µl of the dNTP (2 mM each) mix and 1.2 U of "Hotstar" Taq DNA polymerase (Qiagen). The following program was run: 15 min 95° C., 30 cycles 1 min 95° C., 30 sec 68° C., 1.5 min 72° C., then finally 5 min 72° C. for preparation of complete products).

After cutting with restriction endonuclease EcoRI, the DNA fragment obtained was cloned into vector pBSSK(-) (Stratagene, USA) and verified by sequencing. The resultant plasmid was called pBSPamHNL5ex.

Oligonucleotide Primers:

PCRHNL5-a
5'-
TCGAATTCGAGCTCGGTACCCGGGGATCCTCTAGAAATAATTTTGTTTAA
CTTTAAGAAGGAGATATACATATGGAGAAATCAACAATGTCAGTTATACT
ATTTGTGTTGCATC-3' (SEQ ID No. 10)

PCRHNL5-e
5'-
CGAATTCGCCCTTTCGCATGCTCACATGGACTCTTGAATATTATGAATAG
CCTC-3' (SEQ ID No. 11)

EXAMPLE 6

Construction of Expression Constructs for Heterologous Expression of the HNL5 Gene in *Pichia Pastoris*

DNA of plasmid pBSPamHNL5ex was cut with EcoRI, and the HNL fragment was separated from the vector part by means of preparative gel electrophoresis. After eluting the HNL fragment DNA by means of Qiaex II kit (Qiagen), said fragment was cloned into plasmids pHILD2 and pGAPZ (Invitrogen, San Diego, Calif., USA) via the EcoRI cleavage sites. The correct orientation of the insert toward the promoters was checked with the aid of control cuts. In each case, one clone having a correctly orientated insert was selected and preserved. The correct transitions from vector part to incorporated HNL fragment were verified by sequencing. Said two plasmids for expression in *Pichia pastoris* formed were denoted pHILDPamHNL5a (for inducible expression) and pGAPPamHNL5a (for constitutive expression).

EXAMPLE 7

Inducible Expression of the *Prunus Amygdalus* HNL5 Gene in *Pichia Pastoris*

DNA of plasmid pHILDPamHNL5a was cut with restriction endonuclease Not1 and transformed into *Pichia pastoris* GS115 (Invitrogen, San Diego, Calif., USA). Transformation was carried out according to the protocols of the *Pichia* expression kit (Invitrogen, San Diego, Calif., USA). 100 histidine-prototrophic clones were cultivated in liquid medium (500 ml shaker cultures) according to the protocols of the *Pichia* expression kit and induced with methanol for 48 hours. The cells were removed by centrifugation and suspended with disruption buffer (50 mM Tris-HCl pH 7.6) to an optical density ($OD_{600}$) of 50.0 and disrupted in a "Merckenschlager" homogenizer (Braun, Melsungen, FRG) according to the "glass bead method" (Ausubel et al., Current Protocols in Molecular Biology, Green Publishing Associates and Wiley-Interscience, New York, 1999). Both the culture supernatants and cell lysates were assayed for HNL enzyme activity using a standard activity assay (analogous to WO 97/03204) and using racemic mandelonitrile as substrate. Two clones which showed, in these shaker flask experiments, the best activities in the culture supernatant (*Pichia pastoris* PamHNL5-a37 and *Pichia pastoris* PamHNL5-a4) were selected and preserved. Analysis of the methanol utilization type resulted in the phenotype $Mut^\square$ (good methanol utilization) for *Pichia pastoris* PamHNL5-a37 and the phenotype $Mut^s$ (slow methanol utilization) for *Pichia pastoris* PamHNL5-a4.

EXAMPLE 8

Constitutive Expression of the *Prunus Amygdalus* HNL5 Gene in *Pichia Pastoris*

Plasmid pGAPPamHNL5a was transformed into *P. pastoris* GS115. Transformation was carried out according to the protocols of the *Pichia* expression kit from Invitrogen Corp (San Diego, Calif., USA). Transformants were selected from YPD complete medium plates with 100 mg/l Zeocin. 100 Zeocin-resistant clones were cultivated in in each case 500 ml of YPD complete medium and incubated with shaking at 30° C. for 96 hours. The cells were removed by centrifugation and HNL activity was determined in the culture supernatant. A clone which showed the best activity in the culture supernatant was preserved and denoted *Pichia pastoris* PamHNL5-a2.

EXAMPLE 9

HNL Production in a Laboratory Bioreactor Using a *Pichia Pastoris* Strain Transformed with the *Prunus Amygdalus* HNL5 Gene (Methanol-Inducible Expression System).

*Pichia pastoris* PamHNL5-a37 was grown in a standard laboratory bioreactor (total volume 42 l) in a three-phase process. Said process consisted of a first exponential and a second linear growth phase for biomass formation and a subsequent expression phase for formation of the recombinant *Prunus amygdalus* HNL enzyme, in principle following the method described for the production of recombinant *Hevea brasiliensis* HNL (Hasslacher, M., Schall, M., Hayn, M., Bona, R., Rumbold, K., Luckl, J., Griengl, H., Kohlwein, S. D., Schwab, H.: High level intracellular expression of hydroxynitrile lyase from the tropical rubber tree *Hevea brasiliensis* in microbial hosts. Protein Expression and Purification 11, 61–71, 1997).

In detail, the following conditions were kept to: Chemicals 1.–8., measured for 20 liters and dissolved in 15 liters of water, were initially introduced into the bioreactor and sterilized together with the reactor at 121° C. for 1 hour. After cooling to 29° C., the pH of the medium was adjusted to pH 5.0 with ammonia (chemical 9, initially introduced in a sterile feed bottle). Subsequently, approx. 200 ml of a sterile-filtered trace element solution (chemicals 10–18, appropriate amounts for 20 l) were introduced into the bioreactor via a feed bottle.

The bioreactor prepared in this way was inoculated with 2 liters of preculture which had been cultivated in shaker flasks at 30° C. according to the conditions stated in the manual of the *Pichia* expression kit (Invitrogen Corp., San Diego, Calif., USA). Culturing was carried out at a constant temperature of 29° C. Controlling aeration (between 15 and max. 40 liters of air/min) and stirrer revolutions (between 250 to 500 rpm) maintained the $O_2$ partial pressure at a value above 30% of the saturation concentration. After 21 hours, the biomass had grown to a value in the region of 22 g/l of dry cell mass (DCM). From this time onward, sterile glycerol was metered in in constant small portions at 15 min intervals, and 130 g of glycerol were added per hour. In this, second linear growth phase, it was possible to reach a biomass concentration in the range of 70 g/l DCM over a period of 42 hours.

Subsequently, the third phase was initiated by inducing expression via metering in methanol. In this connection, the methanol content of the culture broth was adjusted to a value of 0.8–1% by weight. At the start of and after two days of induction, in each case another portion of sterile trace element solution (chemicals 10–18, appropriate amounts for 20 l, dissolved in approx. 200 ml of water) was added. After an induction phase of 110 hours, it was possible to obtain an amount of enzyme of 110 U/ml of culture broth. After removing the cells, for example by centrifugation, it is possible to obtain a crude enzyme preparation which can be used directly for biocatalytic conversions.

The following chemicals were used for preparing the culture medium (amount per liter):

Ologonucleotide primers:

| | |
|---|---|
| 1. 85% ortho-phosphoric acid | 21 ml |
| 2. CaSO$_4$ | 0.9 g |
| 3. K$_2$SO$_4$ | 14.3 g |
| 4. MgSO$_4$.7H$_2$O | 12.2 g |
| 5. KOH | |
| (chemicals 1 to 5 | |
| in analytical grade) | |
| 6. Glycerol, technical grade | 50 ml |
| 7. Deionized water, home grade, conductivity | 5.5–9.1 μS/cm |
| 8. Anti-foaming agent 10% Acepol 83E | 1 ml |
| (Carl Becker Chemie | |
| GmbH, Hamburg, Germany) | |
| 9. 25% ammonia, technical grade | |

Trace elements and vitamin H (all chemicals in analytical grade):

| | |
|---|---|
| 10. Biotin | 0.8 mg |
| 11. CuSO$_4$.5H$_2$O | 24.0 mg |
| 12. KI | 0.32 mg |
| 13. MnSO$_4$.H$_2$O | 12.0 mg |
| 14. Na$_2$MoO$_4$.2 H$_2$O | 0.2 mg |
| 15. H$_3$BO$_3$ | 0.08 mg |
| 16. CoCl$_2$ | 2.0 mg |
| 17. ZnSO$_4$.7H$_2$O | 80 mg |
| 18. Fe(II)SO$_4$.7H$_2$O | 260 mg |

EXAMPLE 10

Construction of a clone for expressing the *Prunus amygdalus* HNL5 gene as fusion protein with N-terminal and C-terminal parts of *Aspergillus niger* glucose oxidase.

This construct was designed such that the fusion protein formed is directed into the secretory pathway via the heterologous signal sequence.

In a PCR in a 50 μl mixture in 1×PCR buffer (Qiagen), with in each case 100 pmol of primers Glucox2 and Glucoxct, 10 ng of plasmid pPamHNL5orf as template, 5 μl of dNTP (2 mM each) mix, and 1.2 U of "Hotstar" Taq polymerase (Qiagen), the C-terminal and N-terminal ends of the HNL5 gene were replaced by a sequence derived from glucose oxidase and truncated, respectively (program: 15 min 95° C., 30×: 1 min 95° C., 1 min 68° C., 2 min 72° C., and finally 10 min 72° C.). Finally, in a 2$^{nd}$ PCR in a 50 μl mixture in 1×PCR buffer (Qiagen) with 0.1 μl of product from the first PCR as template, in each case 100 pmol of primers Glucox1 and Glucoxct, 2 μl of dNTP (2 mM each) mix, and 2.5 U of Pwo polymerase (Roche Diagnostics, Mannheim, Germany), (program: 5 min 95° C., 30 times: 1 min 95° C., 0.5 min 68° C., 3 min 72° C. and finally 3 min 72° C.) the 5' region of the gene was completed.

The PCR product was incorporated into plasmid pHILD2 (Invitrogen, San Diego, Calif., USA) after cutting with EcoRI, via EcoRI cleavage sites simultaneously introduced at the ends of the DNA fragment. A clone having the correct orientation of the insert toward the aox promoter of plasmid pHILD2 was verified by sequencing the transition regions from vector to insert and preserved. The plasmid constructed in this way was denoted pHILDPamHNL5gox.

Not1-linearized DNA of plasmid pHILDPamHNL5gox was transformed into the strain *Pichia pastoris* GS115 and also into the protease-deficient strain *Pichia pastoris* SMD1168. From each mixture, several histidine-prototrophic clones were cultured in shaker flasks and HNL activity was determined in the cultured supernatant (standard assay). These experiments were carried out analogously, as described in example 7. It was possible to find in the culture supernatant of some clones HNL activity and thus to state that the signal sequence of the *Aspergillus niger* gox gene is capable of directing the heterologous HNL5 protein, when expressed in *Pichia pastoris*, into the secretory pathway.

Oligonucleotide Primers Used

GLUCOX 1
5'-
CACGAATTCATCATGCAGACTCTCCTTGTGAGCTCGCTTGTGGTCTCCCT
CGCTGCGGCCCTGCCACACTAC-3' (SEQ ID No. 12)

GLUCOX2
5'-
TGCGGCCCTGCCACACTACATCAGGAGCAATGGCATTGAAGCCTACAACG
CCACTGATACAAGCTCGGGAAGGATC-3' (SEQ ID No. 13)

GLUCOXCT
5'-GAATTCGCATGCGGCCGCTCACTGCATTGACCTTTCTTGCAGGATTT
GAAG-3' (SEQ ID No. 14)

The nucleic acid sequence of the DNA fragment for a secretory hybrid protein (PamHNL5xGOX) with HNL activity is depicted in FIG. 4, and the amino acid sequence derived therefrom is represented in FIG. 5. A comparison of the amino acid sequences of *Prunus amygdalus* HNL5 and the hybrid protein PamHNL5xGOX can be found in FIG. 6.

EXAMPLE 11

Recombinant protein with HNL activity, which had been produced using the recombinant strain *Pichia pastoris* PamHNL5-a37, as described in example 9, was subjected to a glycosylation analysis by endoglycosidase digest. For this purpose, 100 ml of the culture supernatant were 10 times concentrated by ultrafiltration (Biomax 30,000 NMWL, Millipore, Bedford, Mass., USA). Samples 1–2 were treated with N-glycosidase F (N-glycosidase F kit, Roche Diagnostics, Mannheim, D).

For samples 4–5, an HNL preparation from almonds from Roche was used, and for samples 6 and 7 the concentrated culture supernatant was treated with endoglycosidase H (Roche Diagnostics, Mannheim, D). All mixtures were carried out in a total volume of 10 μl.

Std. Molecular weight standard from N-glycosidase F kit (5 μl=5 μg)

Sample 1: 2 U of PamHNL5 treated with 2.4 U of enzyme according to the protocol of the kit.

Sample 2: 2 U of PamHNL5 treated with 2.4 U of enzyme according to the protocol of the kit, but without denaturation buffer and without heat denaturation Sample 3: 2 PamHNL5 without treatment Sample 4: 0.25 U of Roche R-HNL preparation grade III from almonds (10.3 U/mg), treated with 2.5 U of N-glycosidase F according to the protocol of the kit Sample 5: 0.25 U of the Roche preparation grade III (10.3 U/mg), untreated Sample 6: 2.4 U of PamHNL5 were incubated with 50 mU of endoglycosidase H in 20 mM phosphate buffer without denaturation at 37° C. for 12 hours.

Sample 7: 2.4 U of PamHNL5 were incubated with 50 mU of endoglycosidase H in 20 mM phosphate buffer, 0.2% SDS, 0.4% mercaptoethanol at 37° C. for 12 hours.

After treatment with the glycosidases, the samples were separated on a 12 percent strength SDS polyacrylamide gel and stained with Coomassie Blue.

These results (see FIG. 7) show that a large part of the oligosaccharides bound to PamHNL5 can be removed by endoglycosidase H even without denaturation of the PamHNL5 protein.

Cleaving off the oligosaccharides leads from a protein smear visible around sizes of from 70 to over 100 kDa to a sharp band at about 60 kDa, corresponding to the calculated molecular weight of a nonglycosylated PamHNL5 protein.

A comparable protein band is not present in the Roche preparation or present only to a negligible extent. In addition, it is impossible to see a significant difference between an untreated protein preparation and a preparation treated with endoglycosidase F. From this finding, it can definitely be stated that the recombinant PamHNL5 enzyme is completely different from the enzyme material obtained from almonds.

EXAMPLE 12

Cloning of a Genomic DNA Fragment Having the Coding Region of the *Prunus Amygdalus* HNL1 Gene.

A genomic DNA fragment having the coding region of the *Prunus amygdalus* HNL1 gene was amplified from genomic almond DNA (preparation, see example 1) with the aid of a PCR using primers mandlp2f (5'-ACTACGAATTCGACCATGGAGAAATCAAC-3') (SEQ ID No. 15) and ecpamHNL1e (5'-CAGAATTCGCCCTTGTGCATGCATCGATTAAAGAACCAAGGATGCTGCTGAC-3') (SEQ ID No. 16).

The amplification was carried out in 50 µl reactions with 1.2 units of "Hotstar" DNA polymerase (Qiagen GmbH, Hilden, Germany), in each case 10 pmol of the two primers, 2 µl of a DNTP mix (5 mM each) and 100 ng of genomic almond DNA in standard PCR buffer (Qiagen GmbH, Hilden, Germany). The following PCR program was used: 15 min 95° C., then 10 cycles of 1 min at 94° C., 1 min 45° C. and 1 min 20 sec at 72° C., followed by 30 cycles of 1 min at 94° C., 1 min at 64° C. and 1 min 20 sec at 72° C. and a final extension step at 72° C. for 5 min.

Analysis of the DNA obtained showed that this PCR produced a plurality of DNA fragments of different sizes. Amplified DNA was separated in a preparative agarose gel. DNA from a band of the size to be expected for the HNL1 gene of approx. 2.1 kb was isolated from said agarose gel (Qiaquick Gel Extraction Kit, Qiagen GmbH, Hilden, Germany). The DNA obtained, after digest with restriction endonuclease EcoRI, was cloned into cloning vector pBSSK (−) (Stratagene Cloning Systems, La Jolla, Calif., USA) via the EcoRI cleavage site. 5 clones with appropriate inserts were isolated and the inserts were sequenced by means of the primer walking strategy. A clone corresponding to the consensus sequence obtained in this way was selected and the contained plasmid was denoted pSKpamHNL1_5_3.

The DNA sequence of the *Prunus amygdalus* HNL1 gene was verified and finally determined by amplifying another genomic DNA fragment using primers mandlp3f (5'-ACTACGAATTCGACCATGGAGAAATCAACAATG-3') (SEQ ID No. 17) and pamHNL1end (5'-ATGCTGCTGACTTGAGGGAATC-3') (SEQ ID No. 18). The amplification was carried out in 50 µl reactions with 2.5 units of "Hotstar" DNA polymerase (Qiagen GmbH, Hilden, Germany), in each case 10 pmol of the two primers, 2 µl of a dNTP mix (5 mM each) and 50 ng of genomic almond DNA in standard PCR buffer (Qiagen GmbH, Hilden, Germany). The following PCR program was used:
15 min 95° C., then 5 cycles of 1 min at 94° C., 30 sec at 55° C. and 2 min at 72° C., then 30 cycles with 1 min at 94° C., 30 sec at 68° C. and 2 min at 72° C. and a final extension step at 72° C. for 7 min.

After fractionation of the PCR product in an agarose gel, a single DNA band was detected.

The PCR product was purified by means of the Qiaquick Gel Extraction Kit (Qiagen GmbH, Hilden, Germany) and directly sequenced by means of the primer walking strategy. The DNA sequence is depicted in FIG. 8. Possible introns were identified by their general 5' and 3' splice sites and their homology to the *Prunus serotina* HNL1 gene. The nucleotides in the regions of the three introns are shown in lower case letters in order to recognize the intron regions. The cloned insert in plasmid pSKpamHNL1_5_3 has the same sequence. The protein sequence of the *Prunus amygdalus* HNL1 protein was derived from the coding region of the DNA sequence and is depicted in FIG. 9.

EXAMPLE 13

0.5 g (3.9 mmol) of octanal was dissolved in 6 ml of tert-butyl methyl ether and 7.5 ml of an aqueous enzyme solution with recombinant R-HNL from example 9 (pH 3.8) were added. After addition of 0.33 ml (8.4 mmol) of hydrocyanic acid, the mixture was vigorously stirred on a magnetic stirrer at room temperature in order to form an emulsion, and the reaction was followed by means of GC on a cyclodextrin column. After a reaction time of 3 hours, cyanohydrin was formed with 81.1% ee and 48% conversion.

EXAMPLE 14

80 ml (34 units/mmol aldehyde) of an aqueous enzyme solution with recombinant R-HNL (34 units/mmol aldehyde) were diluted with 10 ml of 200 mM potassium phosphate/sodium citrate buffer pH 3.8 and added to a solution of 42.2 g (300 mmol) of 2-chlorobenzaldehyde and 42 ml of tert-butyl methyl ether, precooled to 10° C. Subsequently, 19.6 ml (501 mmol) of hydrocyanic acid were metered into the reaction mixture with stirring at 950 rpm within 40 min. After derivatization of cyanohydrin with acetyl chloride, the course of the reaction was followed by means of GC on a cyclodextrin column.

| Hours | % Conversion | % ee |
|-------|--------------|------|
| 3.5   | 71.5         | 90.6 |
| 22    | 99.7         | 90   |

COMPARATIVE EXAMPLE 0.25 to 1 ml of R-oxynitrilase solution (E.C.4.1.2.10; 2187 units/ml) was diluted to 4 ml with 50 mM citrate/phosphate buffer (pH 4.0), and the pH of the enzyme solution was adjusted to pH 4.0, where appropriate, with a few drops of citric acid solution. A solution of 3 ml of tert-butyl methyl ether and 0.8 g (5.69 mmol) of 2-chlorobenzaldehyde was added to said solution and, subsequently, 445 µl (11.38 mmol) of hydrocyanic acid were added. The reaction mixture was stirred at 900 rpm by means of a magnetic stirrer at room temperature.

Conversion and enantiomeric purity of the (R)-cyanohydrin formed were analyzed by means of GC. For this purpose, a sample of the reaction solution was centrifuged and 50 µl of the organic phase were diluted with dichloromethane. After derivatization with acetyl chloride, a gas chromatographic analysis on a cyclodextrin column was carried out.

| | 0.25 ml of enzyme solution corresponding to 96 units/mmol of aldehyde | | 0.5 ml of enzyme solution corresponding to 192 units/mmol of aldehyde | | 1.0 ml of enzyme solution corresponding to 384 units/mmol of aldehyde | |
|---|---|---|---|---|---|---|
| Time (h) | % Conversion | % ee | % Conversion | % ee | % Conversion | % ee |
| 1.5 | 79.1 | 77.5 | 97.6 | 81.6 | 98.7 | 89.4 |
| 3 | 98 | 77.4 | 100 | 81.5 | 100 | 89.1 |

The comparative experiment showed that when using the recombinant proteins of the invention in analogy to example 13 only a tenth of the required amount of native protein is required in order to achieve comparable enantiomeric purities (ee values).

The invention claimed is:

1. An isolated protein having hydroxynitrile lyase activity selected from the group consisting of:
   (1) a protein having hydroxynitrile lyase activity comprising the amino acid sequence of SEQ ID NO: 20;
   (2) a protein having hydroxynitrile lyase activity encoded by a nucleotide sequence having the nucleic acid sequence of SEQ ID NO: 19;
   (3) a protein having hydroxynitrile lyase activity encoded by a nucleotide sequence having at least 85% identity with the nucleic acid sequence of SEQ ID NO: 19;
   (4) a protein having hydroxynitrile lyase activity encoded by a nucleotide sequence having the nucleic acid sequence from nucleotide 13 to nucleotide 2151 of SEQ ID NO: 19; and
   (5) a protein having hydroxynitrile lyase activity encoded by a nucleotide sequence having the nucleic acid sequence of SEQ ID NO: 19 without the intron regions of nucleotides 116 to nucleotide 257, nucleotide 918 to nucleotide 1120, or nucleotide 1962 to nucleotide 2077.

2. The isolated protein of claim 1, wherein the protein is recombinantly produced.

3. The recombinant protein of claim 2 which is obtained by heterologous expression.

4. The recombinant protein of claim 2, which comprises host-specific glycosylation.

5. The recombinant protein of claim 2, wherein the protein is prepared by expression in an eukaryotic microorganism.

6. The recombinant protein of claim 2, wherein said protein is prepared by expression in a fungus.

7. An isolated fusion protein or heterologous protein having hydroxynitrile lyase activity selected from the group consisting of:

(1) a protein having hydroxynitrile lyase activity having the amino acid sequence of SEQ ID NO: 22; and (2) a protein having hydroxynitrile lyase activity encoded by a nucleotide sequence having the nucleic acid sequence of SEQ ID NO: 21 having the 5' and 3' terminal portions of the nucleotide sequence encoding *Aspergillus niger* glucose oxidase protein.

8. An isolated protein having hydroxynitrile lyase activity selected from the group consisting of:

(1) a protein having the amino acid sequence of SEQ ID NO: 24; and (2) a protein encoded by a nucleotide sequence having the nucleic acid sequence of SEQ ID NO: 23.

9. A method for producing (R)- or (S)-cyanohydrins comprising contacting the protein having hydroxynitrile lyase activity of claim 1 with aliphatic, aromatic or heteroaromatic aldehydes and ketones in an organic, aqueous or 2-phase system or in emulsion in the presence of a cyanide group donor.

10. A method for producing (R)- or (S)-cyanohydrins comprising contacting the recombinant protein having hydroxynitrile lyase activity of claim 2 with aliphatic, aromatic or heteroaromatic aldehydes and ketones in an organic, aqueous or 2-phase system or in emulsion in the presence of a cyanide group donor.

11. A method for producing (R)- or (S)-cyanohydrins comprising contacting the fusion protein or heterologous protein having hydroxynitrile lyase activity of claim 7 with aliphatic, aromatic or heteroaromatic aldehydes and ketones in an organic, aqueous or 2-phase system or in emulsion in the presence of a cyanide group donor.

12. A method for producing (R)- or (S)-cyanohydrins comprising contacting the protein having hydroxynitrile lyase activity of claim 8 with aliphatic, aromatic or heteroaromatic aldehydes and ketones in an organic, aqueous or 2-phase system or in emulsion in the presence of a cyanide group donor.

* * * * *

SEQUENCE LISTING

<160> NUMBER OF SEQ ID NOS: 24

<210> SEQ ID NO 1
<211> LENGTH: 35
<212> TYPE: DNA
<213> ORGANISM: Artificial Sequence
<220> FEATURE:
<223> OTHER INFORMATION: Description of the artificial sequence:
      Synthetic oligonucleotide primer

<400> SEQUENCE: 1
cggaattcac aatatggaga aatcaacaat gtcag                          35

<210> SEQ ID NO 2
<211> LENGTH: 33
<212> TYPE: DNA
<213> ORGANISM: Artificial Sequence
<220> FEATURE:
<223> OTHER INFORMATION: Description of the artificial sequence:
      Synthetic oligonucleotide primer

<400> SEQUENCE: 2
cggaattctt cacatggact cttgaatatt atg                            33

<210> SEQ ID NO 3
<211> LENGTH: 64
<212> TYPE: DNA
<213> ORGANISM: Artificial Sequence
<220> FEATURE:
<223> OTHER INFORMATION: Description of the artificial sequence:
      Synthetic oligonucleotide primer

<400> SEQUENCE: 3
gaagatctga attccatgga gaaatcaaca atgtcagtta tactatttgt gttgcatctt   60
cttg                                                              64

<210> SEQ ID NO 4
<211> LENGTH: 68
<212> TYPE: DNA
<213> ORGANISM: Artificial Sequence
<220> FEATURE:
<223> OTHER INFORMATION: Description of the artificial sequence:
      Synthetic oligonucleotide primer

<400> SEQUENCE: 4
ctatttgtgt tgcatcttct tgttcttcat cttcagtatt cagaggttca ctcgcttgcc    60
aatacttc                                                             68

<210> SEQ ID NO 5
<211> LENGTH: 67
<212> TYPE: DNA
<213> ORGANISM: Artificial Sequence
<220> FEATURE:
<223> OTHER INFORMATION: Description of the artificial sequence:
      Synthetic oligonucleotide primer

<400> SEQUENCE: 5
gttcactcgc ttgccaatac ttctgctcat gattttagct acttgaagtt tgtgtacaac    60
gccactg                                                              67

<210> SEQ ID NO 6
<211> LENGTH: 33
<212> TYPE: DNA
<213> ORGANISM: Artificial Sequence
<220> FEATURE:
<223> OTHER INFORMATION: Description of the artificial sequence:
      Synthetic oligonucleotide primer

<400> SEQUENCE: 6
gatgtattgg aagagaagag gatcttctct act                                 33

<210> SEQ ID NO 7
<211> LENGTH: 56
<212> TYPE: DNA
<213> ORGANISM: Artificial Sequence
<220> FEATURE:
<223> OTHER INFORMATION: Description of the artificial sequence:
      Synthetic oligonucleotide primer

<400> SEQUENCE: 7
gatcctcttc tcttccaata catcaaattt gtcagctatt ggagtcatat atacgg        56

<210> SEQ ID NO 8
<211> LENGTH: 66
<212> TYPE: DNA
<213> ORGANISM: Artificial Sequence
<220> FEATURE:
<223> OTHER INFORMATION: Description of the artificial sequence:
      Synthetic oligonucleotide primer

<400> SEQUENCE: 8
caaccggatt gacctttctt gcaggatttg aaggcccaca taccttccta acatcagata    60
gaagcc                                                               66

<210> SEQ ID NO 9
<211> LENGTH: 73
<212> TYPE: DNA
<213> ORGANISM: Artificial Sequence
<220> FEATURE:
<223> OTHER INFORMATION: Description of the artificial sequence:
      Synthetic oligonucleotide primer

<400> SEQUENCE: 9
gaagatctgg aattcttcac atggactctt gaatattatg aatagcctcc aaccggattg    60
acctttcttg cag                                                       73

<210> SEQ ID NO 10
<211> LENGTH: 114

<212> TYPE: DNA
<213> ORGANISM: Artificial Sequence
<220> FEATURE:
<223> OTHER INFORMATION: Description of the artificial sequence:
      Synthetic oligonucleotide primer

<400> SEQUENCE: 10
tcgaattcga gctcggtacc cggggatcct ctagaaataa ttttgtttaa ctttaagaag    60
gagatataca tatggagaaa tcaacaatgt cagttatact atttgtgttg catc         114

<210> SEQ ID NO 11
<211> LENGTH: 54
<212> TYPE: DNA
<213> ORGANISM: Artificial Sequence
<220> FEATURE:
<223> OTHER INFORMATION: Description of the artificial sequence:
      Synthetic oligonucleotide primer

<400> SEQUENCE: 11
cgaattcgcc ctttcgcatg ctcacatgga ctcttgaata ttatgaatag cctc          54

<210> SEQ ID NO 12
<211> LENGTH: 72
<212> TYPE: DNA
<213> ORGANISM: Artificial Sequence
<220> FEATURE:
<223> OTHER INFORMATION: Description of the artificial sequence:
      Synthetic oligonucleotide primer

<400> SEQUENCE: 12
cacgaattca tcatgcagac tctccttgtg agctcgcttg tggtctccct cgctgcggcc    60
ctgccacact ac                                                       72

<210> SEQ ID NO 13
<211> LENGTH: 75
<212> TYPE: DNA
<213> ORGANISM: Artificial Sequence
<220> FEATURE:
<223> OTHER INFORMATION: Description of the artificial sequence:
      Synthetic oligonucleotide primer

<400> SEQUENCE: 13
tgcggccctg ccacactaca tcaggagcaa tggcattgaa gcctacaacg ccactgatac    60
aagctcggaa ggatc                                                    75

<210> SEQ ID NO 14
<211> LENGTH: 51
<212> TYPE: DNA
<213> ORGANISM: Artificial Sequence
<220> FEATURE:
<223> OTHER INFORMATION: Description of the artificial sequence:
      Synthetic oligonucleotide primer

<400> SEQUENCE: 14
gaattcgcat gcggccgctc actgcattga cctttcttgc aggatttgaa g             51

<210> SEQ ID NO 15
<211> LENGTH: 29
<212> TYPE: DNA
<213> ORGANISM: Artificial Sequence
<220> FEATURE:
<223> OTHER INFORMATION: Description of the artificial sequence:
      Synthetic oligonucleotide primer

<400> SEQUENCE: 15

```
actacgaatt cgaccatgga gaaatcaac                                         29
```

<210> SEQ ID NO 16
<211> LENGTH: 52
<212> TYPE: DNA
<213> ORGANISM: Artificial Sequence
<220> FEATURE:
<223> OTHER INFORMATION: Description of the artificial sequence:
      Synthetic oligonucleotide primer

<400> SEQUENCE: 16

```
cagaattcgc ccttgtgcat gcatcgatta agaaccaag gatgctgctg ac               52
```

<210> SEQ ID NO 17
<211> LENGTH: 33
<212> TYPE: DNA
<213> ORGANISM: Artificial Sequence
<220> FEATURE:
<223> OTHER INFORMATION: Description of the artificial sequence:
      Synthetic oligonucleotide primer

<400> SEQUENCE: 17

```
actacgaatt cgaccatgga gaaatcaaca atg                                    33
```

<210> SEQ ID NO 18
<211> LENGTH: 22
<212> TYPE: DNA
<213> ORGANISM: Artificial Sequence
<220> FEATURE:
<223> OTHER INFORMATION: Description of the artificial sequence:
      Synthetic oligonucleotide primer

<400> SEQUENCE: 18

```
atgctgctga cttgagggaa tc                                                22
```

<210> SEQ ID NO 19
<211> LENGTH: 2162
<212> TYPE: DNA
<213> ORGANISM: Prunus amygdalus

<400> SEQUENCE: 19

```
ggaattcaca atatggagaa atcaacaatg tcagttatac tatttgtgtt gcatcttctt       60
gttcttcatc ttcagtattc agaggttcac tcgcttgcca atacttctgc tcatggtaaa      120
tttccatctt cagtattcat ttaacagcaa aatgtgtaga tttataatta agaaaactga      180
cacaagtagt gcaagaaaca agctaattta gatgcatgtt gaaaaaaatc tttcatctct      240
tcacatatat tttgcagatt ttagctactt gaagtttgtg tacaacgcca ctgatacaag      300
ctcggaagga tcatatgact acattgtaat cggtggagga acatcagggt gtccattggc      360
agcaacttta tcagaaaaat acaaggtgct tcttctagaa agaggcacta ttgctacaga      420
atacccgaac acgttgactg cagatggggt tgcatataat ctgcagcaac aagatgatgg      480
aaagacgcca gttgaaaggt tcgtgtccga agatggcatt gataatgtgc gagccaggat      540
cctcggtggc acgaccataa tcaatgcagg cgtctacgcc agagctaaca tttcattcta      600
tagtcaaaca ggaattgaat gggacctgga tttggtcaat aagacatatg agtgggttga      660
agacgccatt gtggtcaagc caaataatca atcttggcaa tctgttatag gagagggatt      720
cttggaggcg ggtattcttc cagacaatgg atttagtttg gatcacgaag caggaactag      780
actcaccggc tcaactttg acaataatgg aacgcgacat gcggctgatg aactgcttaa      840
taaaggagac cctaataact tgctagttgc agttcaggcc tcagtagaga agatcctctt      900
```

-continued

```
ctcttccaat acatcaagta tgttgcatca gtgatattta atggtagctc ctagtttgtc    960
atgctgcact cgaaaattat tattttatca ttttaaaata ctaacagaat agtgtgaagt   1020
ctcatatttc ccttccatat ttcccaaatt tccataaaca aaacttccca attctccttc   1080
gtttagtttg acaataatta taagctattc tctaatgcag atttgtcagc tattggagtc   1140
atatatacgg attctgatgg aaactctcat caggcatttg tacgcggtaa cggagaagtt   1200
attgttagtg cagggacaat cggaacgcct cagcttctac tacttagtgg cgttggacca   1260
gagtcttacc tatcttctct caacatcaca gttgttcagc cgaatcctta tgttgggcag   1320
tttgtgtatg acaatcctcg taatttcatt aatattttgc ccccaaatcc aattgaagcc   1380
tctgttgtaa ctgttttagg cattagaagt gattattatc aagtttctct gtcaagcttg   1440
ccatttttcca ctccacccctt tagtctttttt cctacaacat cttacccccct cccaaattcg   1500
acttttgctc atattgttag ccaagttcca ggaccattgt ctcatggttc tgtcacgcta   1560
aattcatcat ctgacgtgag aatcgctcca aatattaaat tcaattacta ttcaaattcc   1620
acagaccttg ctaattgtgt tagcggcatg aagaagcttg gtgacttatt aaggacaaag   1680
gcattagaac catataaagc tcgagatgtg ctgggaattg acggtttcaa ttatttggga   1740
gtaccttttgc cagagaacca aacagatgat gcatccttcg aaacattttg tctagataat   1800
gtagcttcat actggcatta ccacggtgga agccttgttg ggaaagtgct tgatgacagt   1860
ttccgtgtta tggggatcaa agcattacgc gttgttgatg cctccacttt cccttacgaa   1920
ccaaacagcc atcctcaggg cttctatctg atgttaggaa ggtatgtgat gcacacttcc   1980
aaccactaga gattctcaat attttgttgt tgttgtaatg aactctctgc cgcattgctc   2040
ttttttatta atccttaaaa ttttgtgttt tgcgcaggta tgtgggcctt caaatcctgc   2100
aagaaaggtc aatccggttg gaggctattc ataatattca agagtccatg tgaagaattc   2160
cg                                                                 2162
```

<210> SEQ ID NO 20
<211> LENGTH: 559
<212> TYPE: PRT
<213> ORGANISM: Prunus amygdalus

<400> SEQUENCE: 20

```
Met Glu Lys Ser Thr Met Ser Val Ile Leu Phe Val Leu His Leu Leu
 1               5                  10                  15

Val Leu His Leu Gln Tyr Ser Glu Val His Ser Leu Ala Asn Thr Ser
             20                  25                  30

Ala His Asp Phe Ser Tyr Leu Lys Phe Val Tyr Asn Ala Thr Asp Thr
         35                  40                  45

Ser Ser Glu Gly Ser Tyr Asp Tyr Ile Val Ile Gly Gly Gly Thr Ser
     50                  55                  60

Gly Cys Pro Leu Ala Ala Thr Leu Ser Glu Lys Tyr Lys Val Leu Leu
 65                  70                  75                  80

Leu Glu Arg Gly Thr Ile Ala Thr Glu Tyr Pro Asn Thr Leu Thr Ala
                 85                  90                  95

Asp Gly Phe Ala Tyr Asn Leu Gln Gln Gln Asp Asp Gly Lys Thr Pro
            100                 105                 110

Val Glu Arg Phe Val Ser Glu Asp Gly Ile Asp Asn Val Arg Ala Arg
        115                 120                 125

Ile Leu Gly Gly Thr Thr Ile Ile Asn Ala Gly Val Tyr Ala Arg Ala
    130                 135                 140
```

-continued

```
Asn Ile Ser Phe Tyr Ser Gln Thr Gly Ile Glu Trp Asp Leu Asp Leu
145                 150                 155                 160

Val Asn Lys Thr Tyr Glu Trp Val Glu Asp Ala Ile Val Val Lys Pro
                165                 170                 175

Asn Asn Gln Ser Trp Gln Ser Val Ile Gly Glu Gly Phe Leu Glu Ala
            180                 185                 190

Gly Ile Leu Pro Asp Asn Gly Phe Ser Leu Asp His Glu Ala Gly Thr
        195                 200                 205

Arg Leu Thr Gly Ser Thr Phe Asp Asn Asn Gly Thr Arg His Ala Ala
    210                 215                 220

Asp Glu Leu Leu Asn Lys Gly Asp Pro Asn Asn Leu Leu Val Ala Val
225                 230                 235                 240

Gln Ala Ser Val Glu Lys Ile Leu Phe Ser Ser Asn Thr Ser Asn Leu
                245                 250                 255

Ser Ala Ile Gly Val Ile Tyr Thr Asp Ser Asp Gly Asn Ser His Gln
            260                 265                 270

Ala Phe Val Arg Gly Asn Gly Glu Val Ile Val Ser Ala Gly Thr Ile
        275                 280                 285

Gly Thr Pro Gln Leu Leu Leu Ser Gly Val Gly Pro Glu Ser Tyr
    290                 295                 300

Leu Ser Ser Leu Asn Ile Thr Val Val Gln Pro Asn Pro Tyr Val Gly
305                 310                 315                 320

Gln Phe Val Tyr Asp Asn Pro Arg Asn Phe Ile Asn Ile Leu Pro Pro
                325                 330                 335

Asn Pro Ile Glu Ala Ser Val Val Thr Val Leu Gly Ile Arg Ser Asp
            340                 345                 350

Tyr Tyr Gln Val Ser Leu Ser Ser Leu Pro Phe Ser Thr Pro Pro Phe
        355                 360                 365

Ser Leu Phe Pro Thr Thr Ser Tyr Pro Leu Pro Asn Ser Thr Phe Ala
    370                 375                 380

His Ile Val Ser Gln Val Pro Gly Pro Leu Ser His Gly Ser Val Thr
385                 390                 395                 400

Leu Asn Ser Ser Ser Asp Val Arg Ile Ala Pro Asn Ile Lys Phe Asn
                405                 410                 415

Tyr Tyr Ser Asn Ser Thr Asp Leu Ala Asn Cys Val Ser Gly Met Lys
            420                 425                 430

Lys Leu Gly Asp Leu Leu Arg Thr Lys Ala Leu Glu Pro Tyr Lys Ala
        435                 440                 445

Arg Asp Val Leu Gly Ile Asp Gly Phe Asn Tyr Leu Gly Val Pro Leu
    450                 455                 460

Pro Glu Asn Gln Thr Asp Asp Ala Ser Phe Glu Thr Phe Cys Leu Asp
465                 470                 475                 480

Asn Val Ala Ser Tyr Trp His Tyr His Gly Gly Ser Leu Val Gly Lys
                485                 490                 495

Val Leu Asp Asp Ser Phe Arg Val Met Gly Ile Lys Ala Leu Arg Val
            500                 505                 510

Val Asp Ala Ser Thr Phe Pro Tyr Glu Pro Asn Ser His Pro Gln Gly
        515                 520                 525

Phe Tyr Leu Met Leu Gly Arg Tyr Val Gly Leu Gln Ile Leu Gln Glu
    530                 535                 540

Arg Ser Ile Arg Leu Glu Ala Ile His Asn Ile Gln Glu Ser Met
545                 550                 555
```

<210> SEQ ID NO 21
<211> LENGTH: 1632
<212> TYPE: DNA
<213> ORGANISM: Artificial Sequence
<220> FEATURE:
<223> OTHER INFORMATION: Description of the artificial sequence:
DNA coding for hybrid protein
PamHNL5xGOX

<400> SEQUENCE: 21

| | | | | | |
|---|---|---|---|---|---|
| gaattcatca | tgcagactct | ccttgtgagc | tcgcttgtgg | tctccctcgc | tgcggccctg | 60 |
| ccacactaca | tcaggagcaa | tggcattgaa | gcctacaacg | ccactgatac | aagctcggaa | 120 |
| ggatcatatg | actacattgt | aatcggtgga | ggaacatcag | ggtgtccatt | ggcagcaact | 180 |
| ttatcagaaa | aatacaaggt | gcttcttcta | gaaagaggca | ctattgctac | agaatacccg | 240 |
| aacacgttga | ctgcagatgg | gtttgcatat | aatctgcagc | aacaagatga | tggaaagacg | 300 |
| ccagttgaaa | ggttcgtgtc | cgaagatggc | attgataatg | tgcgagccag | gatcctcggt | 360 |
| ggcacgacca | taatcaatgc | aggcgtctac | gccagagcta | acatttcatt | ctatagtcaa | 420 |
| acaggaattg | aatgggacct | ggatttggtc | aataagacat | atgagtgggt | tgaagacgcc | 480 |
| attgtggtca | agccaaataa | tcaatcttgg | caatctgtta | taggagaggg | attcttggag | 540 |
| gcgggtattc | ttccagacaa | tggatttagt | ttggatcacg | aagcaggaac | tagactcacc | 600 |
| ggctcaactt | ttgacaataa | tggaacgcga | catgcggctg | atgaactgct | taataaagga | 660 |
| gaccctaata | acttgctagt | tgcagttcag | gcctcagtag | agaagatcct | cttctcttcc | 720 |
| aatacatcaa | atttgtcagc | tattggagtc | atatatacgg | attctgatgg | aaactctcat | 780 |
| caggcatttg | tacgcggtaa | cggagaagtt | attgttagtg | cagggacaat | cggaacgcct | 840 |
| cagcttctac | tacttagtgg | cgttggacca | gagtcttacc | tatcttctct | caacatcaca | 900 |
| gttgttcagc | cgaatcctta | tgttgggcag | tttgtgtatg | acaatcctcg | taatttcatt | 960 |
| aatattttgc | ccccaaatcc | aattgaagcc | tctgttgtaa | ctgttttagg | cattagaagt | 1020 |
| gattattatc | aagtttctct | gtcaagcttg | ccattttcca | ctccacccct | tagtcttttt | 1080 |
| cctacaacat | cttaccccct | cccaaattcg | acttttgctc | atattgttag | ccaagttcca | 1140 |
| ggaccattgt | ctcatggttc | tgtcacgcta | aattcatcat | ctgacgtgag | aatcgctcca | 1200 |
| aatattaaat | tcaattacta | ttcaaattcc | acagaccttg | ctaattgtgt | tagcggcatg | 1260 |
| aagaagcttg | gtgacttatt | aaggacaaag | gcattagaac | catataaagc | tcgagatgtg | 1320 |
| ctgggaattg | acggtttcaa | ttatttggga | gtacctttgc | cagagaacca | aacagatgat | 1380 |
| gcatccttcg | aaacattttg | tctagataat | gtagcttcat | actggcatta | ccacggtgga | 1440 |
| agccttgttg | ggaaagtgct | tgatgacagt | tccgtgtta | tggggatcaa | agcattacgc | 1500 |
| gttgttgatg | cctccacttt | cccttacgaa | ccaaacagcc | atcctcaggg | cttctatctg | 1560 |
| atgttaggaa | ggtatgtggg | ccttcaaatc | ctgcaagaaa | ggtcaatgca | gtgagcggcc | 1620 |
| gcatgcgaat | tc | | | | | 1632 |

<210> SEQ ID NO 22
<211> LENGTH: 534
<212> TYPE: PRT
<213> ORGANISM: Artificial Sequence
<220> FEATURE:
<223> OTHER INFORMATION: Description of the artificial sequence:
Hybrid protein PamHNL5xGOX

<400> SEQUENCE: 22

Met Gln Thr Leu Leu Val Ser Ser Leu Val Val Ser Leu Ala Ala Ala

-continued

```
  1               5               10              15
Leu Pro His Tyr Ile Arg Ser Asn Gly Ile Glu Ala Tyr Asn Ala Thr
             20                  25                  30
Asp Thr Ser Ser Glu Gly Ser Tyr Asp Tyr Ile Val Ile Gly Gly Gly
             35                  40                  45
Thr Ser Gly Cys Pro Leu Ala Ala Thr Leu Ser Glu Lys Tyr Lys Val
             50                  55                  60
Leu Leu Leu Glu Arg Gly Thr Ile Ala Thr Glu Tyr Pro Asn Thr Leu
65                  70                  75                  80
Thr Ala Asp Gly Phe Ala Tyr Asn Leu Gln Gln Gln Asp Asp Gly Lys
                 85                  90                  95
Thr Pro Val Glu Arg Phe Val Ser Glu Asp Gly Ile Asp Asn Val Arg
                100                 105                 110
Ala Arg Ile Leu Gly Gly Thr Thr Ile Ile Asn Ala Gly Val Tyr Ala
                115                 120                 125
Arg Ala Asn Ile Ser Phe Tyr Ser Gln Thr Gly Ile Glu Trp Asp Leu
                130                 135                 140
Asp Leu Val Asn Lys Thr Tyr Glu Trp Val Glu Asp Ala Ile Val Val
145                 150                 155                 160
Lys Pro Asn Asn Gln Ser Trp Gln Ser Val Ile Gly Glu Gly Phe Leu
                165                 170                 175
Glu Ala Gly Ile Leu Pro Asp Asn Gly Phe Ser Leu Asp His Glu Ala
                180                 185                 190
Gly Thr Arg Leu Thr Gly Ser Thr Phe Asp Asn Asn Gly Thr Arg His
                195                 200                 205
Ala Ala Asp Glu Leu Leu Asn Lys Gly Asp Pro Asn Asn Leu Leu Val
                210                 215                 220
Ala Val Gln Ala Ser Val Glu Lys Ile Leu Phe Ser Ser Asn Thr Ser
225                 230                 235                 240
Asn Leu Ser Ala Ile Gly Val Ile Tyr Thr Asp Ser Asp Gly Asn Ser
                245                 250                 255
His Gln Ala Phe Val Arg Gly Asn Gly Glu Val Ile Val Ser Ala Gly
                260                 265                 270
Thr Ile Gly Thr Pro Gln Leu Leu Leu Leu Ser Gly Val Gly Pro Glu
                275                 280                 285
Ser Tyr Leu Ser Ser Leu Asn Ile Thr Val Val Gln Pro Asn Pro Tyr
                290                 295                 300
Val Gly Gln Phe Val Tyr Asp Asn Pro Arg Asn Phe Ile Asn Ile Leu
305                 310                 315                 320
Pro Pro Asn Pro Ile Glu Ala Ser Val Val Thr Val Leu Gly Ile Arg
                325                 330                 335
Ser Asp Tyr Tyr Gln Val Ser Leu Ser Ser Leu Pro Phe Ser Thr Pro
                340                 345                 350
Pro Phe Ser Leu Phe Pro Thr Thr Ser Tyr Pro Leu Pro Asn Ser Thr
                355                 360                 365
Phe Ala His Ile Val Ser Gln Val Pro Gly Pro Leu Ser His Gly Ser
                370                 375                 380
Val Thr Leu Asn Ser Ser Ser Asp Val Arg Ile Ala Pro Asn Ile Lys
385                 390                 395                 400
Phe Asn Tyr Tyr Ser Asn Ser Thr Asp Leu Ala Asn Cys Val Ser Gly
                405                 410                 415
Met Lys Lys Leu Gly Asp Leu Leu Arg Thr Lys Ala Leu Glu Pro Tyr
                420                 425                 430
```

```
Lys Ala Arg Asp Val Leu Gly Ile Asp Gly Phe Asn Tyr Leu Gly Val
            435                 440                 445

Pro Leu Pro Glu Asn Gln Thr Asp Asp Ala Ser Phe Glu Thr Phe Cys
        450                 455                 460

Leu Asp Asn Val Ala Ser Tyr Trp His Tyr His Gly Gly Ser Leu Val
465                 470                 475                 480

Gly Lys Val Leu Asp Asp Ser Phe Arg Val Met Gly Ile Lys Ala Leu
                485                 490                 495

Arg Val Val Asp Ala Ser Thr Phe Pro Tyr Glu Pro Asn Ser His Pro
            500                 505                 510

Gln Gly Phe Tyr Leu Met Leu Gly Arg Tyr Val Gly Leu Gln Ile Leu
        515                 520                 525

Gln Glu Arg Ser Met Gln
    530
```

<210> SEQ ID NO 23
<211> LENGTH: 2087
<212> TYPE: DNA
<213> ORGANISM: Prunus amygdalus

<400> SEQUENCE: 23

```
atggagaaat caacaatgtc agctatactg ttggtgttat acattttgt cctccatctt      60
caatattctg aggtccactc gcttgccacg acttctgatc atggtaaatc acttcaaccg    120
taattcaaaa caccaaaaag gcaatcaaaa agaaaacgga aaaaagtgta agaaaagcag    180
atatagacgc ctgcatagat gcatgtgcta tactttta aaaactcttc gtctcttgag     240
attttgcaga ttttagctac ctgagctttg catacgacgc cactgatcta gagttggaag    300
gatcatatga ctacgttata gttggcggag gaacatcagg gtgtccattg gcagcaactt    360
tatcagaaaa atacaaggtg ctcgttctcg aaaggggcag tcttccgaca gcatatccca    420
acgtcttgac tgcagatggg tttgtatata atctccagca agaagatgat ggaaagacac    480
cggtcgaaag gttcgtgtcc gaagatggta ttgataatgt acggggcagg gtgctcggtg    540
gcacaagcat tatcaatgcc ggtgtctacg ccagagctaa caccctcaatc tatagtgcat    600
caggagttga ttgggacatg gatttggtta atcagacata tgagtgggtt gaagacacta    660
ttgtgtacaa gccaaattct caatcttggc agtctgttac aaaaactgca ttcttggagg    720
ctggtgttca tccaaaccat ggatttagtt tagatcatga agaaggaact agaattaccg    780
gctcaacttt tgacaacaag ggaacgagac atgcagctga tgaacttctt aataaggaa     840
actctaacaa cttgcgagtt ggagttcatg cctcagtaga aagatcatc ttctccaatg     900
caccaggtat gttgcatcat gcactccaaa attaatattt tgtcatttta aaacactagc    960
aggagccaag gtctggaagt acgaataaaa tttcattatt tccttggat tgttttgata    1020
atgattataa gcttttctgt aatgtaggtt tgacagctac aggagtcata tatagggatt    1080
ctaatggaac gcctcaccaa gcatttgtac gcagtaaggg agaagttatc gtgagtgcag    1140
ggacaattgg gaccccctcaa cttctactac ttagcggtgt tgggccagag tcttacctat    1200
catctctaaa tattccagtt gttctttccc atccttacgt cggacagttt ctgcatgaca    1260
atcctcgtaa tttcattaac attttgcccc caaatccaat tgaacccaca attgtaactg    1320
ytctaggcat ttcaaacgat ttctaccaat gttctttctc gagcttgcca tttacaactc    1380
cacccttcgg tttttttccct agtgcatctt atcccctgcc aaattcgact tttgctcact    1440
ttgctagcaa agtggcagga cctttatcat atggttctct cacactgaaa tcatcctcca    1500
```

```
atgtgagagt cagtccaaat gtcaaattta attactattc aaatctgaca gatctttctc   1560
attgtgttag cggcatgaag aagattggtg aactcttgag cacagacgca ttaaaaccat   1620
ataaagttga agatttgccg ggtgtagaag gttttaatat tttgggaatc cctttgccaa   1680
aggaccaaac agatgatgca gccttcgaaa cattttgccg agaatcagta gcctcatatt   1740
ggcactacca cggtggatgc cttgttggaa aggtgcttga tggtgatttc cgtgttacag   1800
ggatcaatgc attacgcgtt gttgatggct caacattccc ttacacacca gcgagccacc   1860
ctcaggcttt ctatctgatg ttagggaggt atgttacaaa ttctcaataa ttatttggtt   1920
gagtggcttg tttgtaatga actctatgcc atatttctct ttctcatcct ttccattttt   1980
gtgccatggg caggtatgtg gcattaaaa ttctgcaaga aagatcagct tcagatctaa    2040
aaatcttgga ttccctcaag tcagcagcat ccttggttct ttaaact                 2087
```

<210> SEQ ID NO 24
<211> LENGTH: 563
<212> TYPE: PRT
<213> ORGANISM: Prunus amygdalus

<400> SEQUENCE: 24

```
Met Glu Lys Ser Thr Met Ser Ala Ile Leu Leu Val Leu Tyr Ile Phe
  1               5                  10                  15

Val Leu His Leu Gln Tyr Ser Glu Val His Ser Leu Ala Thr Thr Ser
             20                  25                  30

Asp His Asp Phe Ser Tyr Leu Ser Phe Ala Tyr Asp Ala Thr Asp Leu
         35                  40                  45

Glu Leu Glu Gly Ser Tyr Asp Tyr Val Ile Val Gly Gly Gly Thr Ser
     50                  55                  60

Gly Cys Pro Leu Ala Ala Thr Leu Ser Glu Lys Tyr Lys Val Leu Val
 65                  70                  75                  80

Leu Glu Arg Gly Ser Leu Pro Thr Ala Tyr Pro Asn Val Leu Thr Ala
                 85                  90                  95

Asp Gly Phe Val Tyr Asn Leu Gln Gln Glu Asp Asp Gly Lys Thr Pro
            100                 105                 110

Val Glu Arg Phe Val Ser Glu Asp Gly Ile Asp Asn Val Arg Gly Arg
        115                 120                 125

Val Leu Gly Gly Thr Ser Ile Ile Asn Ala Gly Val Tyr Ala Arg Ala
    130                 135                 140

Asn Thr Ser Ile Tyr Ser Ala Ser Gly Val Asp Trp Asp Met Asp Leu
145                 150                 155                 160

Val Asn Gln Thr Tyr Glu Trp Val Glu Asp Thr Ile Val Tyr Lys Pro
                165                 170                 175

Asn Ser Gln Ser Trp Gln Ser Val Thr Lys Thr Ala Phe Leu Glu Ala
            180                 185                 190

Gly Val His Pro Asn His Gly Phe Ser Leu Asp His Glu Glu Gly Thr
        195                 200                 205

Arg Ile Thr Gly Ser Thr Phe Asp Asn Lys Gly Thr Arg His Ala Ala
    210                 215                 220

Asp Glu Leu Leu Asn Lys Gly Asn Ser Asn Asn Leu Arg Val Gly Val
225                 230                 235                 240

His Ala Ser Val Glu Lys Ile Ile Phe Ser Asn Ala Pro Gly Leu Thr
                245                 250                 255

Ala Thr Gly Val Ile Tyr Arg Asp Ser Asn Gly Thr Pro His Gln Ala
            260                 265                 270
```

```
Phe Val Arg Ser Lys Gly Glu Val Ile Val Ser Ala Gly Thr Ile Gly
            275                 280                 285

Thr Pro Gln Leu Leu Leu Leu Ser Gly Val Gly Pro Glu Ser Tyr Leu
        290                 295                 300

Ser Ser Leu Asn Ile Pro Val Val Leu Ser His Pro Tyr Val Gly Gln
305                 310                 315                 320

Phe Leu His Asp Asn Pro Arg Asn Phe Ile Asn Ile Leu Pro Pro Asn
                325                 330                 335

Pro Ile Glu Pro Thr Ile Val Thr Val Leu Gly Ile Ser Asn Asp Phe
                340                 345                 350

Tyr Gln Cys Ser Phe Ser Ser Leu Pro Phe Thr Thr Pro Pro Phe Gly
            355                 360                 365

Phe Phe Pro Ser Ala Ser Tyr Pro Leu Pro Asn Ser Thr Phe Ala His
        370                 375                 380

Phe Ala Ser Lys Val Ala Gly Pro Leu Ser Tyr Gly Ser Leu Thr Leu
385                 390                 395                 400

Lys Ser Ser Ser Asn Val Arg Val Ser Pro Asn Val Lys Phe Asn Tyr
                405                 410                 415

Tyr Ser Asn Leu Thr Asp Leu Ser His Cys Val Ser Gly Met Lys Lys
                420                 425                 430

Ile Gly Glu Leu Leu Ser Thr Asp Ala Leu Lys Pro Tyr Lys Val Glu
            435                 440                 445

Asp Leu Pro Gly Val Glu Gly Phe Asn Ile Leu Gly Ile Pro Leu Pro
450                 455                 460

Lys Asp Gln Thr Asp Asp Ala Ala Phe Glu Thr Phe Cys Arg Glu Ser
465                 470                 475                 480

Val Ala Ser Tyr Trp His Tyr His Gly Gly Cys Leu Val Gly Lys Val
                485                 490                 495

Leu Asp Gly Asp Phe Arg Val Thr Gly Ile Asn Ala Leu Arg Val Val
                500                 505                 510

Asp Gly Ser Thr Phe Pro Tyr Thr Pro Ala Ser His Pro Gln Gly Phe
            515                 520                 525

Tyr Leu Met Leu Gly Arg Tyr Val Gly Ile Lys Ile Leu Gln Glu Arg
        530                 535                 540

Ser Ala Ser Asp Leu Lys Ile Leu Asp Ser Leu Lys Ser Ala Ala Ser
545                 550                 555                 560

Leu Val Leu
```